(12) United States Patent
Oshima et al.

(10) Patent No.: US 10,864,198 B2
(45) Date of Patent: *Dec. 15, 2020

(54) METHODS OF PREVENTING CARDIOVASCULAR EVENTS IN RESIDUAL RISK DYSLIPIDEMIC POPULATIONS

(71) Applicant: Kowa Company, Ltd., Aichi (JP)

(72) Inventors: Ryu Oshima, Tokyo (JP); Gary Gordon, Morrisville, NC (US)

(73) Assignee: Kowa Company, Ltd., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/663,784

(22) Filed: Jul. 30, 2017

(65) Prior Publication Data

US 2018/0028505 A1 Feb. 1, 2018

Related U.S. Application Data

(60) Provisional application No. 62/368,245, filed on Jul. 29, 2016, provisional application No. 62/462,574, filed on Feb. 23, 2017.

(51) Int. Cl.
| | | |
|---|---|---|
| *A61K 31/423* | (2006.01) | |
| *A61K 31/366* | (2006.01) | |
| *A61K 31/40* | (2006.01) | |
| *A61K 31/47* | (2006.01) | |
| *A61K 31/505* | (2006.01) | |
| *A61K 31/41* | (2006.01) | |
| *A61K 9/00* | (2006.01) | |
| *A61K 45/06* | (2006.01) | |

(52) U.S. Cl.
CPC .......... *A61K 31/423* (2013.01); *A61K 9/0053* (2013.01); *A61K 31/366* (2013.01); *A61K 31/40* (2013.01); *A61K 31/41* (2013.01); *A61K 31/47* (2013.01); *A61K 31/505* (2013.01); *A61K 45/06* (2013.01)

(58) Field of Classification Search
CPC .... A61K 31/423; A61K 31/40; A61K 31/505; A61K 31/366; A61K 31/47
See application file for complete search history.

(56) References Cited

U.S. PATENT DOCUMENTS

| | | | |
|---|---|---|---|
| 7,109,226 B2 | 9/2006 | Yamazaki et al. | |
| 8,426,455 B2 | 4/2013 | Takizawa et al. | |
| 2010/0069433 A1* | 3/2010 | Takizawa ............. | A61K 31/423 514/311 |

OTHER PUBLICATIONS

Lambert, Ed. ("Practice Guidelines: ACC/AHA Release Updated Guideline on the Treatment of Blood Cholesterol to Reduce ASCVD Risk"; 2014; American Family Physician; 90(4): 261-265 (Year: 2014).*

Ginsberg et al.; "Effects of Combination Lipid Therapy in Type 2 Diabetes Mellitus"; 2010; N. Engl. J. Med.; 362(17): 1563-1574 (Year: 2010).*

Ishibashi et al.; "Effects of K-877, a novel selective PPARα modulator (SPPARMα), in dyslipidaemic patients: A randomized, double blind, active- and placebo-controlled, phase 2 trial"; Feb. 2016; Atherosclerosis; 249:36-43 (Year: 2016).*

ACC/AHA Release Updated Guideline on the Treatment of Blood Cholesterol to Reduce ASCVD Risk; American Family Physician; vol. 90, No. 4; Aug. 15, 2014.

Summary Minutes of the Endocrinologic and Metabolic Drugs Advisory Committee Hilton Hotel Washington DC/Silver Spring, Maryland; May 19, 2011.

Eric Colman, MD; FDA Advisory Committee Meeting Trilipix® & The ACCORD-Lipid Trial Division of Metabolism and Endocrinology Products U.S. Food and Drug Administration May 19, 2011.

Meeting Roster: Endocrinologic and Metabolic Drugs Advisory Food and Drug Administration Center for Drug Evaluation and Research; Endocrinologic and Metabolic Drugs Advisory Committee; Thursday, May 19, 2011.

Ginsberg, et al. Evolution of the Lipid Trial Protocol of the Action to Control Cardiovascular Risk in Diabetes (ACCORD) Trial; The American Journal of Cardiology; vol. 99 (12A) Jun. 18, 2007.

Supplementary Appendix 1; Supplement to: The ACCORD Study Group. Effects of combination lipid therapy in type 2 diabetes mellitus. N Engl J Med 2010;362:1563-74. DOI: 10.1056/NEJMoa1001282. (PDF last updated Apr. 28, 2010.).

Supplementary Appendix 2; Supplement to: The ACCORD Study Group. Effects of combination lipid therapy in type 2 diabetes mellitus. N Engl J Med 2010;362:1563-74. DOI: 10.1056/NEJMoa1001282: Action to Control Cardiovascular Risk in Diabetes (ACCORD) Trial Protocol.

The ACCORD study (The ACCORD Study Group, Effects of Combination Lipid Therapy in Type 2 Diabetes Mellitus; N Engl J Med 2010;362(17):1563-74.

Action to Control Cardiovascular Risk in Diabetes (ACCORD) trial: design and methods; Am J Cardiol. Jun. 18, 2007;99(12A):21i-33i. Epub Apr. 16, 2007. (Abstract).

Arai, et al. Efficacy and Safety of K-877, Selective Peroxisome Proliferator-Activated Receptor α Modulator (SPPARM1), in Combination With Statin Treatment: Two Randomized, Double-Blind, Placebo-Controlled Clinical Trials in Patients with Dyslipidaemia; K-877 Study Group; 2016.

Tenenbaum, et al. Bezafibrate for the Secondary Prevention of Myocardial Infarction in Patients With Metabolic Syndrome; (Reprinted) Arch Intern Med/vol. 165, May 23, 2005.

(Continued)

*Primary Examiner* — Timothy P Thomas
(74) *Attorney, Agent, or Firm* — Clark G. Sullivan

(57) ABSTRACT

The present invention provides pharmacological interventions for the treatment of dyslipidemia, and to the reduction of residual risk of cardiovascular disease and adverse cardiovascular events in patients on intense statin use or with well-controlled LDL-C concentrations. In particular, the invention relates to the use of pemafibrate to prevent cardiovascular events in populations at-risk due to risk factors such as type 2 diabetes mellitus with dyslipidemia in spite of intense statin use or well-controlled LDL-C.

29 Claims, 10 Drawing Sheets

(56) References Cited

OTHER PUBLICATIONS

Compagnone, et al. Chirospecific of (+) Pilocarpine; Department of Chemistry, University of California; Nov. 26, 1985.
Elam, et al. The ACCORD-Lipid study: implications for treatment of dyslipidemia in Type 2 diabetes mellitus; Clin Lipidol. 2011; 6(1): 9-20. doi:10.2217/clp.10.84.
The FIELD study: The FIELD Study Investigators, Effects of long-term fenofibrate therapy on cardiovascular events in 9795 people with type 2 diabetes mellitus: randomised controlled trial; Lancet 2005; 366: 1849-61.
Scott, et al. Effects of Fenofibrate Treatment on Cardiovascular Disease Risk in 9,795 Individuals With Type 2 Diabetes and Various Components of the Metabolic Syndrome; Diabetes Care, vol. 32, No. 3; pp. 493-498, Mar. 2009.
Jean-Charles Fruchart; Selective peroxisome proliferator-activated receptora modulators (SPPARMα): The next generation of peroxisome proliferator-activated receptor α-agonists; Fruchart Cardiovascular Diabetology 2013, 12:82, pp. 1-8.
Frick MH, et al. Helsinki Heart Study: Primary-prevention trial with gemfibrozil in middle-age men with dyslipidemia; The New England Journal of Medicine; vol. 317(20): 1237-1245; Nov. 12, 1987.
Effects of Extended-Release Niacin with Laropiprant in High-Risk Patients; N Engl J Med 2014;371:203-12.
Nakamura, et al. Stereochemical Control on Yeast Reduction of α-Keto Esters. Reduction by Immobilized Bakers' Yeast in Hexane; J. Org. Chem., vol. 53, No. 11, pp. 2589-2593; 1988.
Romanelli, et al. Synthesis and Enantioselectivity of the Enantiomers of PG9 and SM21, New Potent Analgesic and Cognition-Enhancing Drugs; Chirality 8:225-233 (1996).
Saha, et al. The role of fibrates in the prevention of cardiovascular disease—a pooled meta-analysis of long-term randomized placebo-controlled clinical trials; American Heart Journal, vol. 154(5): 943-953.
Statin-Fibrate Report: Focus on Safety VHA Pharmacy Benefits Management-Strategic Healthcare Group and The Medical Advisory Panel; Sep. 2004.
Rubins et al. Diabetes, Plasma Insulin, and Cardiovascular Disease: subgroup analysis from the Department of Veterans Affairs high-density lipoprotein intervention trial {VAHIT); Arch Intern Med. 2002; 162:2597-2604.
Anthony S. Wierzbicki; Fibrates: no ACCORD on their use in the treatment of dyslipidaemia; Current Opinion in Lipidology 2010, 21:352-358.
Yamazaki, et al. Enantioselective Synthesis of the PPARα Agonist (R)-K-13675 via (S)-2-Hydroxybutyrolactone; Synthesis 2008, No. 7, pp. 1017-1022.
Davidson, MH et al., The FIRST Study: Effects of Fenofibric Acid on Carotid Intima-Media Thickness in Patients With Mixed Dyslipidemia on Atorvastatin Therapy: Randomized, Placebo-Controlled Study (FIRST), Arterioscler Thromb Vasc Biol. 2014;34:1298-1306.
Supplement: The FIRST Study, Davidson, MH et al., Results from the Fenofibric Acid on Caritid Intima-Media Thickness in Subjects with Type IIb Dyslipidemia with Residual Risk in Addition to Atorvastatin Therapy (FIRST) Trial (no date).
The AIM HIGH Investigators, Niacin in Patients with Low HDL Cholesterols Receiving Intensive Statin Therapy, N Engl J Med. Dec. 15, 2011; 365(24):2255-67; HPS2-THRIVE Collaborative Group.
Jellinger, et al. American Association of Clinical Endocrinologists and American College of Endocrinology Guidelines for Management of Dyslipidemia and Prevention of Cardiovascular Disease; AACE 2017 Guidelines; Endocrine Practice vol. 23 (Suppl 2) Apr. 2017; pp. 1-87.
White, et al. Darapladib for Preventing Ischemic Events in Stable Coronary Heart Disease; N Engl J Med 2014;370:1702-11.
Berglund, et al. Evaluation and Treatment of Hypertriglyceridemia: An Endocrine Society Clinical Practice Guideline; Journal of Clinical Endocrinology & Metabolism, Sep. 2012, 97: 2969-2989.

Lincoff, et al. Evacetrapib and Cardiovascular Outcomes in High-Risk Vascular Disease; N Engl J Med 2017; 376:1933-42.
Landray, et al. Effects of Extended-Release Niacin with Laropiprant in High-Risk Patients; N Engl J Med 2014; 371:203-12.
ClinicalTrials.gov, Pemafibrate to Reduce Cardiovascular OutcoMes by Reducing Triglycerides IN patiENts With diabeTes (PROMINENT).
HDL Europe PMC Funders Group, Major Lipids, Apolipoproteins, and Risk of Vascular Disease The Emerging Risk Factors Collaboration. JAMA. Nov. 11, 2009; 302(18): 1993-2000.
US FDA, 22612 Federal Register / vol. 81, No. 74 / Monday, Apr. 18, 2016.
Giraldez et al., Baseline Low-Density Lipoprotein Cholesterol Is an Important Predictor of the Benefit of Intensive Lipid-Lowering Therapy. JACC vol. 52, No. 11, Sep. 9, 2008:914-20.
Grundy et al., Implications of Recent Clinical Trials for the National Cholesterol Education Program Adult Treatment Panel III Guidelines. Circulation Jul. 13, 2004.
Harchaoui et al., Triglycerides and Cardiovascular Risk. Current Cardiology Reviews, 2009, 5, 216-222.
Frick et al., Helsinki Heart Study, NEJM vol. 317 No. 20, No. 12, 1987.
Katz, FDA: Evidentiary Standards for Drug Development and Approval. NeuroRx, vol. 1, No. 3, 2004.
Hounslow et al., Pemafibrate has High Bioavailability and is Principally Excreted by the Liver. Abstract P5.053. Atherosclerosis Supplements 32, 2018 1-162.
Kinoshota et al., Japan Atherosclerosis Sosiety (JAS) Guidelines for Prevention of Atherosclerotic Cardiovascular Diseases 2017. J Atherosclero Thromb 2018; 25: 000-000.
Iwata et al., 2014 AHA Late-Breaking Basic Science Abstracts | Circulation Research. The Novel PPARα Selective Agonist K-877 Suppresses Proinflammatory Pathways and Experimental Arterial Lesion Formation. Abstract 24160.
Ishibashi et al., Efficacy and safety of pemafibrate (K-877), a selective peroxisome proliferator-activated receptor a modulator, in patients with dyslipidemia: Results from a 24-week, randomized, double blind, active-controlled, phase 3 trial. Journal of Clinical Lipidology (2018) 12, 173-184.
Jun et al., Effects of fibrates on cardiovascular outcomes: a systematic review and meta-analysis. www.thelancet.com vol. 375 May 29, 2010.
Kapur et al., Clinical efficacy and safety of statins in managing cardiovascular risk. Vascular Health and Risk Management 2008:4(2) 341-353.
Yokote et al., Long-Term Efficacy and Safety of Pemafibrate, a Novel Selective Peroxisome Proliferator-Activated Receptor-Modulator (SPPARM), in Dyslipidemic Patients with Renal Impairment Int. J. Mol. Sci. 2019, 20, 706.
Kuhnast et al., Innovative pharmaceutical interventions in cardiovascular disease: Focusing on the contribution of non-HDL-C/LDL-C-lowering versus HDL-C-raising: A systematic review and meta-analysis of relevant preclinical studies and clinical trials. European Journal of Pharmacology 763 (2015) 48-63.
Lambert et al., ACC/AHA Release Updated Guideline on the Treatment of Blood Cholesterol to Reduce ASCVD Risk. American Family Physician. vol. 90, No. 4, Aug. 15, 2014.
Matsuba et al., Effects of a novel selective peroxisome proliferator-activated receptor-a modulator, pemafibrate, on hepatic and peripheral glucose uptake in patients with hypertriglyceridemia and insulin resistance. J Diabetes Investig 2018; 9: 1323-1332.
Nakagawa et al., Asymmetric hydrolysis of 2-hydroxy-carboxylic esters using *Escherichia coli*. Tetrahedron Asymmetry 18 (2007) 2394-2398.
Navarese et al., Association Between Baseline LDL-C Level and Total and Cardiovascular Mortality After LDL-C Lowering A Systematic Review and Meta-analysis. JAMA. 2018;319(15):1566-1579.
Pradhan et al., Rationale and design of the Pemafibrate to Reduce Cardiovascular Outcome by Reducing Triglycerides in Patients with Diabetes (PROMINENT) study. American Heart Journal vol. 206, No. 0. 2018.

(56) References Cited

OTHER PUBLICATIONS

Kastelein et al., K-877, a selective PPAR alpha modulator (SPPARM alpha), ameliorates dyslipidaemia in patients with well-controlled LDL Cholesterol levels on statin therapy, without increases in serum creatinine. Abstract P5983. Bedside. Treatment of hypercholesterolemia. A vision to the future. Sep. 1, 2015.
Moutzouri et al., Management of dyslipidemias with fibrates, alone and in combination with statins: role of delayed-release fenofibric acid. Vascular Health and Risk Management 2010:6 525-539.
Silverman et al., Association Between Lowering LDL-C and Cardiovascular Risk Reduction Among Different Therapeutic Interventions A Systematic Review and Meta-analysis. JAMA. 2016;316(12):1289-1297.
The AIM-HIGH Investigators, Niacin in Patients with Low HDL Cholesterol Levels Receiving Intensive Statin Therapy. N Engl J Med 365;24 Dec. 15, 2011.
The FIELD study investigators, Effects of long-term fenofibrate therapy on cardiovascular events in 9795 people with type 2 diabetes mellitus (the FIELD study): randomised controlled trial. www.thelancet.com vol. 366 Nov. 26, 2005.
The HPS2-Thrive Collaborative Group, Effects of Extended-Release Niacin with Laropiprant in High-Risk Patients. N Engl J Med 371;3 Jul. 17, 2014.
Tricor Prescribing Information 2004.
US FDA, Trilipix Risk Benefit Summary 2008.
US FDA, Trilipix Summary Review 2008.
US FDA Letter to Abbot Laboratories, NDA 022224/S-005, 006, Sep. 30, 2011.
Trilipix Prescribing Information 2008.
Trilipix Prescribing Information 2018.
Rubins et al., Gemfibrozil for the Secondary Prevention of Coronary Heart Disease in Men With Low Levels of High-Density Lipoprotein Cholesterol NEJM, vol. 341 No. 6, 411, 1999.
Yamamoto et al., Molecular association model of PPARa and its new specific and efficient ligand, pemafibrate: Structural basis for SPPARMa. Biochemical and Biophysical Research Communications 499 (2018) 239-245.
Yamashita et al., Effects of pemafibrate (K-877) on cholesterol efflux capacity and postprandial hyperlipidemia in patients with atherogenic dyslipidemia. Journal of Clinical Lipidology (2018) 12, 1267-1279.
Iwata et al., Novel PPARα selective agonist K-877 suppresses macrophage activation and experimental arterial lesion formation (Poster presented at 2015 meeting of ESC).
Ishibash et al., Benefical Effects of K-877, a Highly Potent and Selective PPARa Agonist, on Plasma Lipoprotein Profile in Patients With Atherogenic Dyslipidemia (Poster presented at 2012 meeting of EAS).
Arai et al., Jnl Atherscler Thromb 2018; 2015: 521-538.
Kastelein et al., K-877, a selective PPAR alpha modulator (SPPARM alpha), improves dyslipidaemia in statin-treated patients with type 2 diabetes mellitus (Aug. 5, 2015 e-poster).
Kastelein et al., K-877, a selective PPAR alpha modulator (SPPARM alpha), ameliorates dyslipidaemia in patients with well-controlled LDL-cholesterol levels on statin therapy, without increases in serum creatinine (Aug. 5, 2015 e-poster).
Ishibashi et al., Efficacy and Safety of K-877, a Potent and Selective PPAR-α Agonist, in Japanese Patients With Dyslipidemia (Poster presented at 2013 meeting of AHA).
Yamashita et al., Comparison of the Effects of Novel Peroxisome Proliferator-Activated Receptor Alpha Agonist K-877 and Fenofibrate on High-Density Lipoprotein Subclass Distribution Determined by High-Performance Liquid Chromatography in Patients With Dyslipidemia (Poster presented at 2013 Meeting of AHA).
Ishibashi et al, Suppression of Postprandial Triglyceride, Remnant-Like Particles-Cholesterol (RLP-C) and APOB48 Surge by K-877, a Highly Potent and Selective PPARa Agonist (Poster presented at 2012 Meeting of EAS).
Araki et al, A Highly Potent and Specific PPAR Alpha Agonist, K-877, Improves Lipid Profiles and Insulin Sensitivity in Dislipidemia Subjects; An Integrated Analysis of 3 Phase 2/3 Trials. (Poster presented at 2014 meeting of EASD).
Yokote et al., Marked Increase of Plasma Fibroblast Growth Factor 21 in Dyslipidemic Patients Treated With K-877, a Novel Highly Potent and Specific Peroxisome Proliferator-Activated Receptor Alpha Agonist (Poster presented at 2013 meeting of AHA).
Raymond et al., Cleve Clin J Med. Jan. 2014 ; 81(1): 11-19.
Extended European Search report issued in corresponding European Application No. 17183806.3 dated Oct. 25, 2017.
Ishibashi et al. "Effects of K-877, 877, a novel selective PPAR[alpha] modulator (SPPARM[alpha]), in dyslipidaemic patients: A randomized, double blind, active- and placebo-controlled, phase 2 trial", Atherosclerosis, Elsevier, Amsterdam, NL, vol. 249 , Feb. 26, 2016 (Feb. 26, 2016), pp. 36-43.
Yamazaki, et al. Design and synthesis of highly potent and selective human peroxisome proliferator-activated receptor agonists; Bioorganic & Medicinal Chemistry Letters 17 (2007) 4689-4693.
Fruchart; Selective peroxisome proliferator-activated receptora modulators (SPPARMα): The next generation of peroxisome proliferator-activated receptor α-agonists; Cardiovascular Diabetology 2013, 12:82; pp. 1-8.
Fruchart et al. Residual macrovascular risk in 2013: what have we learned? Cardiovascular Diabetology 2014, 13:26; pp. 1-17.
Sahebkar, et al. New peroxisome proliferator-activated receptor agonists: potential treatments for atherogenic dyslipidemia and non-alcoholic fatty liver disease; Expert Opinion. Pharmacather (2014) 15(4):493-503.
Van Capelleveen, et al. Novel Therapies Focused on the High-Density Lipoprotein Particle; Circ Res. 2014; 114:193-204.
Sahebkar et al. Role of Selective Peroxime Proliferator active selective modulators in managing cardiometabolic disease: tale of a roller-coaster. Diabetes Obesity and Metabolism 16:780-792, 2014.
Pawlak, et al. Molecular mechanism of PPARa action and its impact on lipid metabolism, inflammation and fibrosis in non-alcoholic fatty liver disease; Journal of Hepatology 2015 vol. 62, 720-733.
Liu, et al. Early investigational drugs targeting PPAR-a for the treatment of metabolic disease; Expert Opin. Investig. Drugs (2015) 24(5):611-621.
Sairyo, et al. A Novel Selective PPARa Modulator (SPPARMa), K-877 (Pemafibrate), Attenuates Postprandial Hypertriglyceridemia in Mice, J Atheroscler Tromb, 2017; 24:1-11.
Nordestgaard, et al. A New Start for Triglycerides and Remnant Cholesterol-Nonfasting, Clinical Chemistry 63:8, pp. 1418-1419 (2017).
Raza-Iqbal, et al. Transcriptome Analysis of K-877 (a Novel Selective PPARα Modulator (SPPARMα))-Regulated Genes in Primary Human Hepatocytes and the Mouse Liver. Journal of Atherosclerosis and Thrombosis, 2015, vol. 22, No. 8; 754-772.
Doi, A Novel Selective PPARα Modulator. Journal of Atherosclerosis and Thrombosis; 2015, vol. 22, No. 8; 750-751.
Colin, et al. Emerging Small Molecule Drugs; Handbook of Exp. Pharmacol. 2015; 617-630.
Ishibashi, et al. Effects of K-877, a novel selective PPARa modulator (SPPARMa), in dyslipidaemic patients: A randomized, double blind, active- and placebo-controlled, phase 2 trial; Atherosclerosis 249 (2016) 36-43.
Hennuyer, et al. The novel selective PPARa modulator (SPPARMa) pemafibrate improves dyslipidemia, enhances reverse cholesterol transport and decreases inflammation and atherosclerosis; Atherosclerosis 249 (2016) 200-208.
Camejo; Selective PPAR modulators (SPPARs) may fill the need for treatment of the atherogenic dyslipidemia of insulin resistance and type 2 diabetes: Can they reduce the associated cardiac risk? Atherosclerosis 249 (2016) 224-225.
Nakamura et al. Postprandial hyperlipidemia as a potential residual risk factor; Journal of Cardiology 67 (2016) 335-339.
Bell, et al. Contemporary and Novel Therapeutic Options for Hypertriglyceridemia. Clinical Therapeutics/vol. 37, No. 12, 2015; pp. 2732-2750.
Gryn, et al. New oral agents for treating dyslipidemia, Curr Opin Lipidol 2016, 27:579-584.
Barter et al. New Era of Lipid-Lowering Drugs; Pharmacol Rev 68:458-475, Apr. 2016.

(56) References Cited

OTHER PUBLICATIONS

Z. Gajdosik, Pemafibrate; Drugs of the Future, 2016, 41(2):111-121.
Takei, et al. Selective peroxisome proliferator-activated receptor-a modulator K-877 efficiently activates the peroxisome proliferator-activated receptor-a pathway and improves lipid metabolism in mice; J Diabetes Investig 2017; 8: 446-452.
Han, et al. PPARs: regulators of metabolism and as therapeutic targets in cardiovascular disease. Part I: PPAR-a, Future Cardiol. 2017, 13(3), 259-278.
Badimon, CETP inhibition and HDL: what is the trial REVEALing? Cardiovascular Research (2018) 114, e15-e16.
Davidson et al. The future of n-3 polyunsaturated fatty acid therapy, Curr Opin Lipidol 2016, 27(6):570-578.
Honda, et al., Pemafibrate, a novel selective peroxisome proliferator-activated receptor alpha modulator, improves the pathogenesis in a rodent model of nonalcoholic steatohepatitis. Scientific Reports, 7:42477, pp. 1-11 (2017).
Honda, et al., Pemafibrate, a novel selective peroxisome proliferator-activated receptor alpha modulator, improves the pathogenesis in a rodent model of nonalcoholic steatohepatitis. Scientific Reports, 7:42477, pp. 1-11 (2017) (Supplement).
Takei, et al. Effects of K-877, a novel selective PPARa modulator, on small intestine contribute to the amelioration of hyperlipidemia in low-density lipoprotein receptor knockout mice; Journal of Pharmacological Sciences 133 (2017) 214-222.
Zeljko Reiner, Hypertriglyceridaemia and risk of coronary artery disease, Nature Reviews: Cardiology, 2017, vol. 14:401-411.
Ferri, et al. PPAR-α agonists are still on the rise: an update on clinical and experimental findings; Opinion on Investigational Drugs, 26:5, 593-602 (2017).
Mello, et al. PPARs and Mitochondrial Metabolism: From NAFLD to HCC, PPAR Research, vol. 2016, Article ID 7403230, 18 pages.
Arai, et al. Efficacy and safety of K-877, a novel selective peroxisome proliferatoractivated receptor a modulator (SPPARMa), in combination with statin treatment: Two randomised, double-blind, placebo-controlled clinical trials in patients with dyslipidaemia, Atherosclerosis 261 (2017) 144-152.
Nikolic, et al. PPAR Agonists, Atherogenic Dyslipidemia and Cardiovascular Risk, Current Pharmaceurital Design, 2017, 23, 894-902.
Maki, et al. Renoprotective effect of a novel selective PPARα modulator K-877 in db/db mice: A role of diacylglycerol-protein kinase C-NAD(P)H oxidase pathway Metabolism Clinical and Experimental 71 (2017) 33-45).
ACC/AHA 2013 ACC/AHA Guideline on the Treatment of Blood Cholesterol to Reduce Atherosclerotic Cardiovascular Risk in Adults.
Grundy, et al. 2018 Cholesterol Clinical Practice Guidelines. A Report of the American College of Cardiology/American Heart Association Task Force on Clinical Practice Guidelines.
Miller et al., Triglycerides and Cardiovascular Disease A Scientific Statement From the American Heart Association. Circulation. 2011;123:2292-2333.
Araki et al., Effects of Pemafibrate, a Novel Selective PPARα Modulator, on Lipid and Glucose Metabolism in Patients With Type 2 Diabetes and Hypertriglyceridemia: A Randomized, Double-Blind, Placebo-Controlled, Phase 3 Trial Diabetes Care 2018;41:538-546 (Supplement).
Araki et al., Effects of Pemafibrate, a Novel Selective PPARα Modulator, on Lipid and Glucose Metabolism in Patients With Type 2 Diabetes and Hypertriglyceridemia: A Randomized, Double-Blind, Placebo-Controlled, Phase 3 Trial Diabetes Care 2018;41:538-546.
Araki et al., The Peroxisome Proliferator-Activated Receptor (PPAR-alpha) Agonist Pemafibrate Protects against Diet-Induced Obesity in Mice. Int. J. Mol. Sci. 2018, 19, 2148.
Armitage, Cholesteryl Ester Transfer Protein Inhibition for Preventing Cardiovascular Events. Journal of the American College of Cardiology vol. 73, No. 4, 2019.
The BIP Study Group, Secondary Prevention by Raising HDL Cholesterol and Reducing Triglycerides in Patients With Coronary Artery Disease the Bezafibrate Infarction Prevention (BIP) Study. Circulation Jul. 4, 2000.
Bruckert et al., Comparison of the Efficacy of Simvastatin and Standard Fibrate Therapy in the Treatment of Primary Hypercholesterolemia and Combined Hyperlipidemia. Clin. Cardiol. 18.621-629 (1995).
Canner et al., Fifteen Year Mortality in Coronary Drug Project Patients: Long-Term Benefit With Niacin. IACC vol. 8, No. 6 Dec. 1986:1245-55.
Cholesterol Treatment Trialists' (CTT) Collaborators, The effects of lowering LDL cholesterol with statin therapy in people at low risk of vascular disease: meta-analysis of individual data from 27 randomised trials. Lancet. Aug. 11, 2012; 380(9841): 581-590.
European Medicines Agency, Guideline on multiplicity issues in clinical trials. Dec. 15, 2016.

* cited by examiner

Change from baseline to Week 12 in TG with pemafibrate versus placebo in dyslipidemia patients receiving statin treatment. The graph reports left to right 0.05 mg BID, 0.1 mg BID, 0.2 mg BID, 0.1 mg QD, 0.2 mg QD, and 0.4 mg QD pemafibrate.

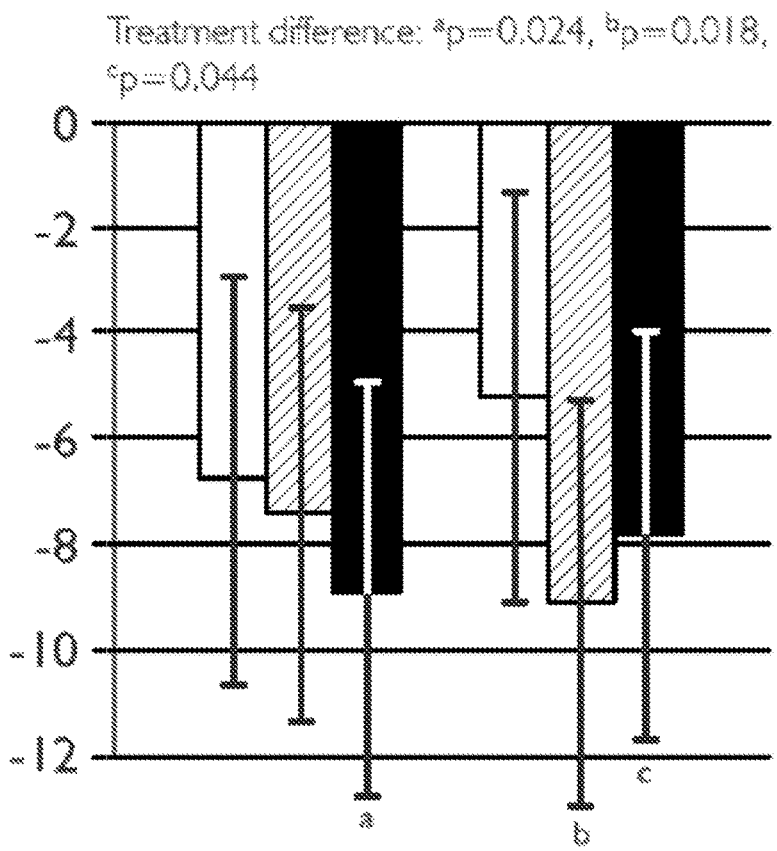
Change from baseline to Week 12 in non-HDL-C with pemafibrate versus placebo in dyslipidemia patients receiving statin treatment. The graph reports left to right 0.05 mg BID, 0.1 mg BID, 0.2 mg BID, 0.1 mg QD, 0.2 mg QD, and 0.4 mg QD pemafibrate.

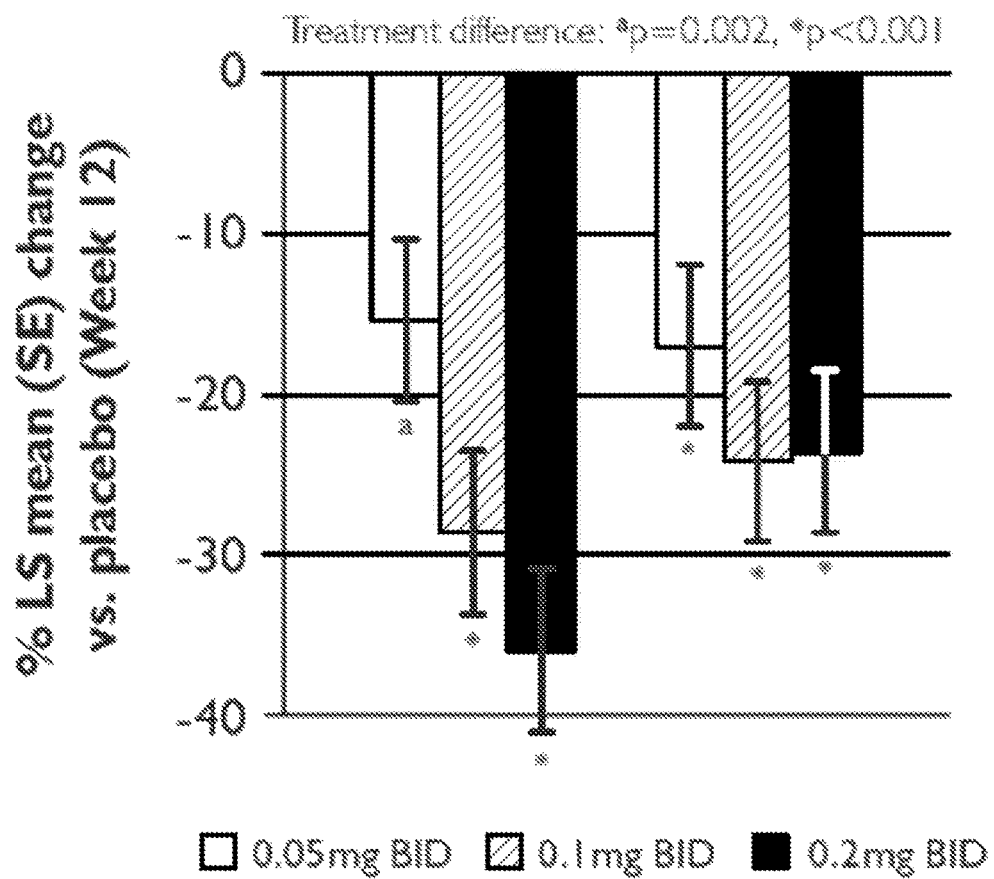
Change from baseline to Week 12 in Apo CIII with pemafibrate versus placebo in dyslipidemia patients receiving statin treatment. The graph reports left to right 0.05 mg BID, 0.1 mg BID, 0.2 mg BID, 0.1 mg QD, 0.2 mg QD, and 0.4 mg QD pemafibrate.

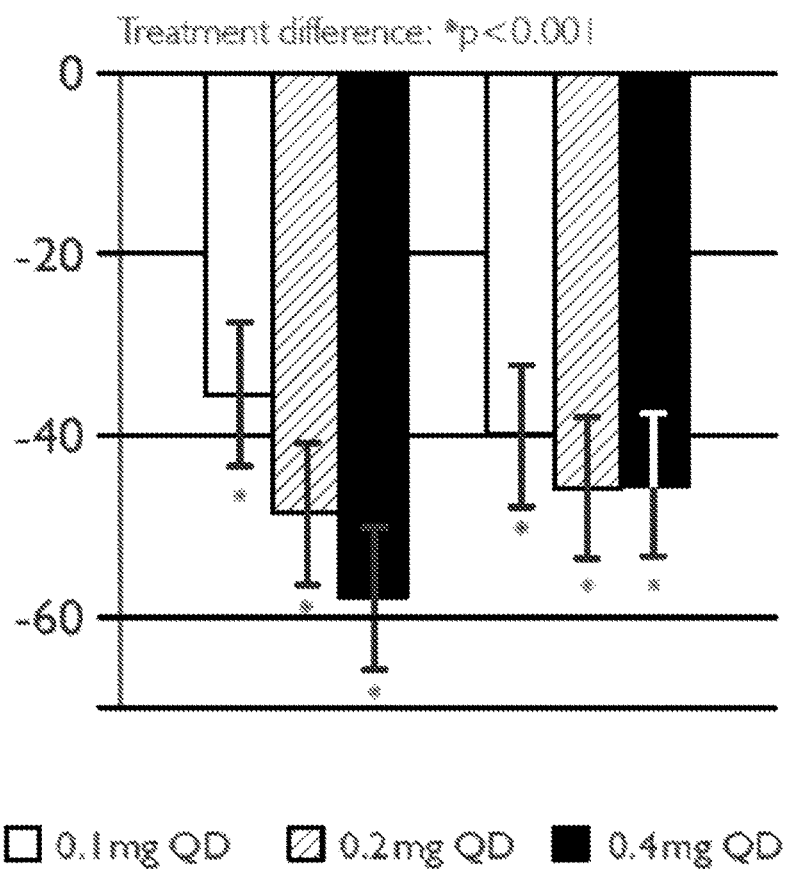
Change from baseline to Week 12 in remnant-C with pemafibrate versus placebo in dyslipidemia patients receiving statin treatment. The graph reports left to right 0.05 mg BID, 0.1 mg BID, 0.2 mg BID, 0.1 mg QD, 0.2 mg QD, and 0.4 mg QD pemafibrate.

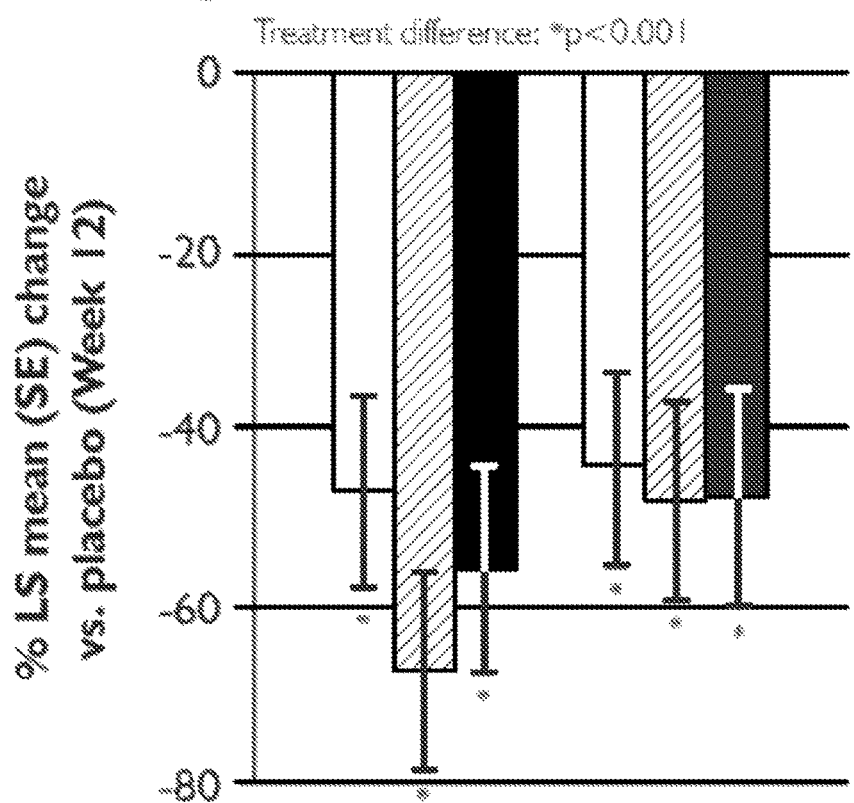
Change from baseline to Week 12 in TG with pemafibrate versus placebo in dyslipidemia patients receiving statin treatment with type 2 diabetes mellitus. The graph reports left to right 0.05 mg BID, 0.1 mg BID, 0.2 mg BID, 0.1 mg QD, 0.2 mg QD, and 0.4 mg QD pemafibrate.

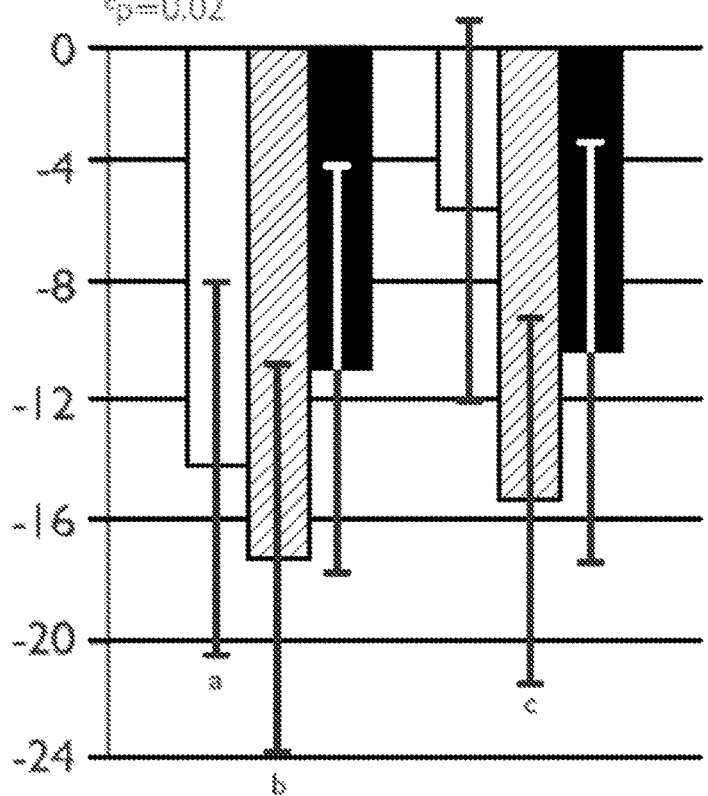
Change from baseline to Week 12 in non-HDL-C with pemafibrate versus placebo in dyslipidemia patients receiving statin treatment with type 2 diabetes mellitus. The graph reports left to right 0.05 mg BID, 0.1 mg BID, 0.2 mg BID, 0.1 mg QD, 0.2 mg QD, and 0.4 mg QD pemafibrate.

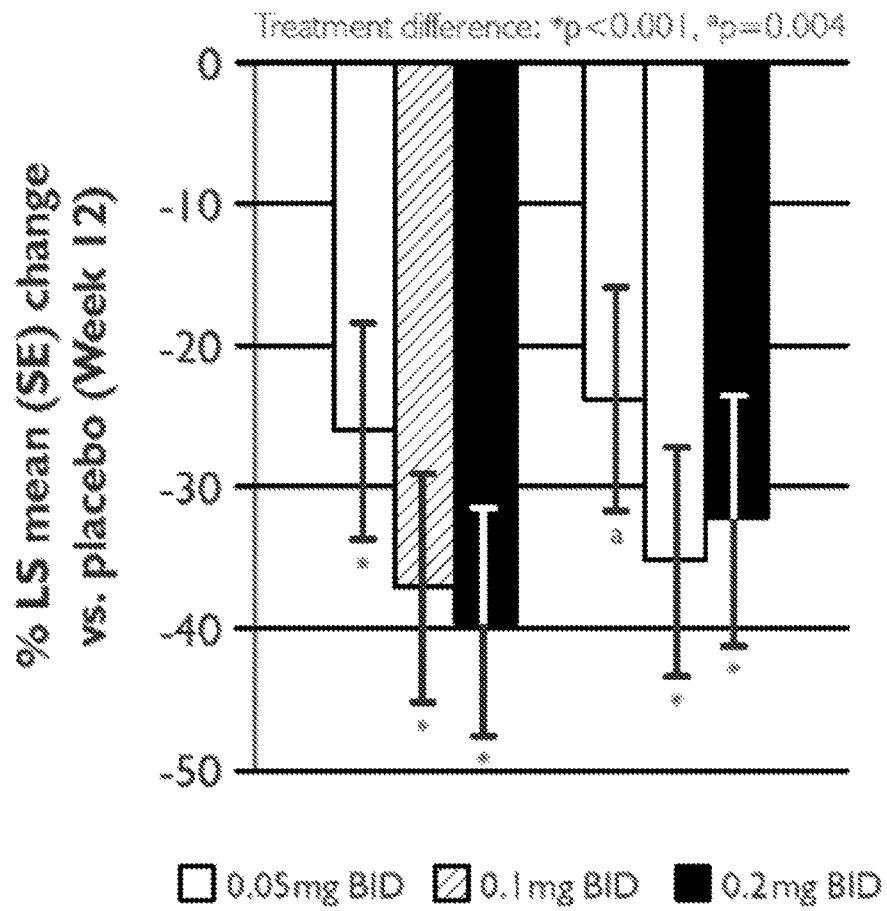
Change from baseline to Week 12 in Apo CIII with pemafibrate versus placebo in dyslipidemia patients receiving statin treatment with type 2 diabetes mellitus. The graph reports left to right 0.05 mg BID, 0.1 mg BID, 0.2 mg BID, 0.1 mg QD, 0.2 mg QD, and 0.4 mg QD pemafibrate.

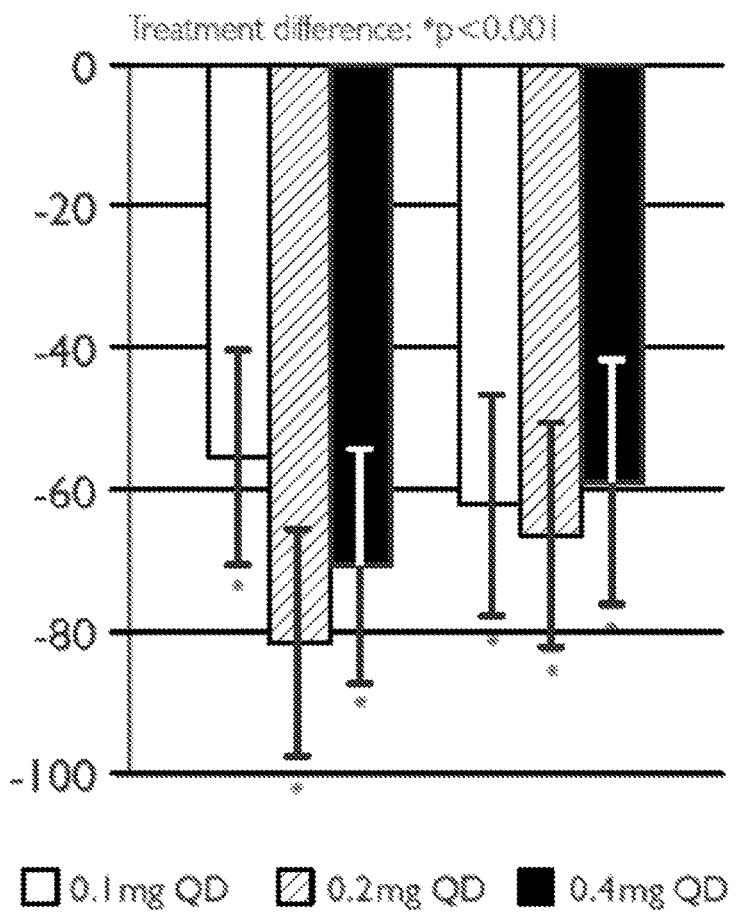
Change from baseline to Week 12 in remnant-C with pemafibrate versus placebo in dyslipidemia patients receiving statin treatment with type 2 diabetes mellitus. The graph reports left to right 0.05 mg BID, 0.1 mg BID, 0.2 mg BID, 0.1 mg QD, 0.2 mg QD, and 0.4 mg QD pemafibrate.

Percent change (95% CI) in TG from baseline (B.L.) to Week 12

Percent Change from Baseline (BL) to Week 12
Left to right doses: placebo, 0.1, 0.2 and 0.4 mg/day pemafibrate BID Percent Change (SD) from Baseline
Doses from left to right: placebo, 0.1, 0.2, and 0.4 mg/day pemafibrate BID Mean change (SD) from baseline to week 12 in fasting plasma glucose (A) and HOMA-IR (B)
Doses from left to right: placebo, 0.1, 0.2 and 0.4 mg/day pemafibrate BID

METHODS OF PREVENTING CARDIOVASCULAR EVENTS IN RESIDUAL RISK DYSLIPIDEMIC POPULATIONS

PRIOR APPLICATIONS

This application claims priority to U.S. Provisional Patent Application Nos. 62/368,245 (filed Jul. 29, 2016) and 62/462,574 (filed Feb. 23, 2017). The contents of these applications is hereby incorporated by reference.

FIELD OF THE INVENTION

The present invention relates to pharmacological interventions for the treatment of residual dyslipidemia, and to the reduction of residual cardiovascular risk in patients on certain moderate or intense statin therapies or with otherwise controlled LDL-C concentrations.

BACKGROUND OF THE INVENTION

Cardiovascular diseases ("CVDs") are a group of disorders of the heart and circulatory system that include coronary heart disease ("CHD"), cerebrovascular disease, peripheral arterial disease, rheumatic heart disease, congenital heart disease, deep vein thrombosis and pulmonary embolism. Despite significant advances in medical treatments, CVDs remain the number one cause of death globally. An estimated 17.5 million people died from CVDs in 2012, representing 31% of all global deaths. Dyslipidemia is one of the primary risk factors for CVDs.

Dyslipidemia is an imbalance in a person's lipid metabolism, such that one or more of the person's lipid values are associated with an increased risk of CVDs. Dyslipidemia is particularly prevalent in type 2 diabetes patients and other patients at high risk for CVDs. Dyslipidemia is typically characterized by one or a combination of elevated levels of low-density lipoprotein cholesterol ("LDL-C" or "LDL"), elevated triglyceride ("TG") levels, or low levels of high-density lipoprotein cholesterol ("HDL-C" or "HDL"), the so-called "good cholesterol." Pharmacological therapies aimed at treating dyslipidemia are one of the principal tools employed by physicians to reduce the risk of CVDs.

The Third Report of the National Cholesterol Education Program ("NCEP") Expert Panel on Detection, Evaluation, and Treatment of High Blood Cholesterol in Adults (Adult Treatment Panel III) discloses lipid cut-points for evaluating cardiovascular risk. Under these cut-points, a person having an LDL-C concentration greater than 100 mg/dL (2.59 mmol/L) is at risk for a cardiovascular event. A person having a total cholesterol concentration greater than 200 mg/dL (5.18 mmol/L) is at risk for a cardiovascular event. A person having an HDL-C concentration less than 40 mg/dL (1.0 mmol/L) for men and less than 50 mg/dL (1.3 mmol/L) for women is at risk for a cardiovascular event. A person having a fasting triglyceride concentration greater than 150 mg/dL (1.70 mmol/L) is at risk for cardiovascular events. A person having a non-HDL-C concentration greater than 130 mg/dL (3.37 mmol/L) is also at risk for a cardiovascular event.

Despite these well-publicized lipid cut-points and associated cardiovascular risk, pharmacotherapies directed at these lipids have had a mixed record in controlled clinical trials. The use of statins to reduce LDL-C concentrations is well-accepted as the first line treatment for preventing adverse cardiovascular events in dyslipidemic patients. However, statins do not completely eliminate all cardiovascular risk, particularly in populations who remain dyslipidemic based on lipids other than LDL-C. This "residual risk" population has proven especially difficult to treat.

Niacin's failure to treat this residual risk population has been particularly well documented. Even though niacin lowers elevated triglycerides, a known risk factor for cardiovascular disease, and increases low HDL-C, another known risk factor for cardiovascular disease, it was unable to prevent cardiovascular events in two clinical trials of patients who, despite being on statins, had residual cardiovascular risk. See The AIM HIGH Investigators, *Niacin in Patients with Low HDL Cholesterols Receiving Intensive Statin Therapy*, N ENGL J MED. 2011 Dec. 15; 365(24):2255-67; HPS2-THRIVE Collaborative Group. *Effects of extended-release niacin with laropiprant in high-risk patients*. N ENGL J MED. 2014 Jul. 17; 371(3):203-12.

Fibrates are another class of molecules that modify lipid profiles. The ability of fibrates, including clofibrate, bezafibrate, gemfibrozil and fenofibrate, to lower elevated triglycerides and increase low HDL-C concentrations by acting on the peroxisome proliferator-activated receptor ("PPAR"), has been well-documented. However, the biochemical and clinical effects produced by these molecules can differ significantly. Two published clinical studies involving gemfibrozil, "The Helsinki Heart Study" (Frick M H et al., *Helsinki Heart Study: primary-prevention trial with gemfibrozil in middle-aged men with dyslipidemia. Safety of treatment, changes in risk factors, and incidence of coronary heart disease*. N ENGL J MED 1987; 317:1237-45), and "The VA-HIT Study" (Rubins H B et al., *Diabetes, plasma insulin, and cardiovascular disease: subgroup analysis from the Department of Veterans Affairs high-density lipoprotein intervention trial* (VA-HIT). ARCH INTERN MED 2002; 162: 2597-604), met their primary endpoint for reducing cardiovascular risk, while fenofibrate study results have been much less promising.

The FIELD study (The FIELD Study Investigators, *Effects of long-term fenofibrate therapy on cardiovascular events in 9795 people with type 2 diabetes mellitus*, LANCET 2005; 366:1849-1861) enrolled 9795 people aged 50-75 years with type 2 diabetes mellitus and not taking statin therapy at study entry, treated them for five years with placebo or fenofibrate, and did not show a benefit in its primary endpoint of major coronary events, although it did show some potential benefit in its secondary endpoints. The ACCORD study (The ACCORD Study Group, *Effects of Combination Lipid Therapy in Type 2 Diabetes Mellitus*, N ENGL J MED 2010; 362:1563-1574) investigated whether fenofibrate in combination with a statin, as compared with statin monotherapy, would reduce the risk of cardiovascular disease in patients with type 2 diabetes mellitus. The primary outcome was the first occurrence of nonfatal myocardial infarction, nonfatal stroke, or death from cardiovascular causes. The study did not detect a significant treatment effect in its primary endpoint or in any of its secondary endpoints.

The FIRST Study (Davidson, M H et al., *Effects of Fenofibric Acid on Carotid Intima-Media Thickness in Patients With Mixed Dyslipidemia on Atorvastatin Therapy: Randomized, Placebo-Controlled Study* (FIRST), ARTERIOSCLER THROMB VASC BIOL. 2014; 34:1298-1306) produced similarly disappointing results. There, the investigators studied whether adding a fibrate to statin therapy would reduce residual cardiovascular risk associated with elevated triglycerides and low high-density lipoprotein cholesterol, by reducing progression of carotid intima-media thickness ("cIMT"), and did not observe any improvement in cIMT over statin monotherapy.

The role of diabetes/metabolic syndrome on the efficacy of lipid lowering therapies also is poorly understood. While some clinicians believe that fibrates are more likely to benefit this group than less risk populations, the effect of fibrates on lipid parameters can be less in this patient population. For example, the authors of the VA-HIT trial (supra) reported at page 2604: "It is also interesting to note that the clinical efficacy of gemfibrozil was more pronounced in subjects with diabetes than those without despite the fact that gemfibrozil's effects on lipids was less pronounced (i.e. lesser reduction in triglyceride level and lesser increase in HDL-C level in diabetic compared to non-diabetic persons). Other studies have also noted a possible lesser effect of gemfibrozil on HDL-C and triglyceride levels in persons with diabetes compared with those without." These results, and the negative results for niacin, raise serious questions as to whether fibrates are able to reduce cardiovascular risk by increasing HDL-C and/or lowering triglycerides.

Given the residual cardiovascular risk that continues in many patients on statin therapy, and the equivocal often conflicting results observed in clinical trials, there remains a need to develop new lipid modifying drugs with different biochemical activities, and to identify populations of patients likely to benefit from such drugs. Pemafibrate (a/k/a K-877) is a new fibrate under development by Kowa Company, Ltd. for treating dyslipidemia and preventing adverse cardiovascular events. Pemafibrate is a PPARα activator that is much more potent at affecting lipid metabolism and is more specific for the PPARα receptor than other fibrates. Fruchart J C, *Selective peroxisome proliferator-activated receptorα modulators (SPPARMα): The next generation of peroxisome proliferator-activated receptor α-agonists*, CARDIOVASCULAR DIABETOLOGY 2013, 12:82, at Table 1 reports the following effects of PPAR agonists on PPAR transcriptional activity:

| Compound | | Aleglitazar [26] | GFT505 [48] | K-877 [52] | Fenofibrate [26, 52] |
|---|---|---|---|---|---|
| PPARα | EC$_{50}$ (nM) | 5 | 10 to 20 | 1 | 14,000 [52]; 22,400 [26] |
| PPARγ | EC$_{50}$ (nM) | 9 | NA | 2,300 | ~100,000 |
| PPARδ | EC$_{50}$ (nM) | 376 | 100 to 150 | 1,000 | not activated |

EC50 effective concentration inducing 50% response;
NA not available.

The ability of pemafibrate to reduce cardiovascular risk has not been studied in clinical trials, and populations best suited for treatment by pemafibrate have not been published.

Pharmacological therapies are needed that can alter lipid parameters in a beneficial way, particularly in patients with type 2 diabetes, or those presenting with residual risk of cardiovascular events in spite of statin treatment, to lower the risk of adverse cardiovascular events. Better definitions of populations likely to benefit from such therapies are also needed, based on lipid profiles and cardiovascular risk.

It is therefore an object of the present invention to provide pemafibrate therapies that can reduce cardiovascular risk in patients with one or more risk factors for cardiovascular events, particularly in patients with well-controlled LDL-C concentrations or on intense statin therapy.

Another object of the present invention is to reduce cardiovascular risk in populations at risk for adverse cardiovascular events due to an imbalanced lipid metabolism, particularly in patients with well-controlled LDL-C concentrations or on intense statin therapy.

Another object of the present invention is to reduce cardiovascular risk in populations at risk for adverse cardiovascular events due to an imbalanced lipid metabolism, particularly in patients with type 2 diabetes mellitus.

Other objects of the present invention are to identify at-risk patients likely to benefit from pemafibrate treatment and to define specific subjects for such treatment.

Still another object is to treat dyslipidemia in patients with elevated TG and low HDL-C concentrations, particularly residual dyslipidemia in patients on intense statin therapy or have well-controlled LDL-C concentrations.

SUMMARY OF THE INVENTION

Despite previous failures of fenofibrate to reduce cardiovascular risk in two well-publicized clinical trials, and the failure of both niacin and fenofibrate to reduce cardiovascular risk when added to statin therapy, the inventors have surprisingly determined that pemafibrate will reduce cardiovascular risk, particularly when employed in a well-defined dyslipidemic population of patients on moderate to high intensity statin therapy or otherwise controlled LDL-C concentrations. Thus, in a first principal embodiment the invention provides a method of preventing an adverse cardiovascular event in a patient with type 2 diabetes mellitus comprising administering to the patient therapeutically effective amounts of pemafibrate and a statin, wherein: (a) the statin is selected from moderate to high intensity statin therapy, or non-moderate to high intensity statin therapy if the patient has an LDL-C concentration ≤70 mg/dL; (b) the patient has an HDL-C concentration ≤40 mg/dL; and (c) the patient has a fasting TG concentration ≥200 mg/dL and <500 mg/dL; and the method prevents the cardiovascular event.

The methods of the present invention produce several unexpected benefits not previously seen with fibrate therapies. In particular, the present methods are effective in primary and secondary prevention. Thus, in a second principal embodiment the invention provides a method of preventing an adverse cardiovascular event in a patient with type 2 diabetes mellitus without systemic atherosclerosis or cardiovascular disease comprising administering to the patient therapeutically effective amounts of pemafibrate and a statin, wherein: (a) the statin is selected from moderate to high intensity statin therapy, or non-moderate to high intensity statin therapy if the patient has an LDL-C concentration ≤70 mg/dL; (b) the patient has an HDL-C concentration ≤40 mg/dL; (c) the patient has a fasting TG concentration ≥200 mg/dL and <500 mg/dL; and (d) the method prevents the cardiovascular event.

In a third principal embodiment the invention provides a method of preventing an adverse cardiovascular event in a patient with type 2 diabetes mellitus and a HbA1c concentration greater than 8.1% comprising administering to the patient therapeutically effective amounts of pemafibrate and a statin, wherein: (a) the statin is selected from moderate to high intensity statin therapy, or non-moderate to high intensity statin therapy if the patient has an LDL-C concentration ≤70 mg/dL; (b) the patient has an HDL-C concentration ≤40 mg/dL; (c) the patient has a fasting TG concentration ≥200 mg/dL and <500 mg/dL; and (d) the method prevents the cardiovascular event.

Another aspect of the invention relates to the clinical endpoints at which the treatments are directed. Even though meta-analyses have found that fibrates are only effective for preventing non-fatal myocardial infarction, Saha S A et al. *The role of fibrates in the prevention of cardiovascular disease: a pooled meta-analysis of long-term randomized*

*placebo-controlled clinical trials.* AM HEART J 2007; 154: 943-953, the methods of the present invention are also directed at nonfatal ischemic stroke, hospitalization for unstable angina requiring unplanned coronary revascularization, or cardiovascular death. Thus, in a fourth principal embodiment the invention provides a method of preventing an adverse cardiovascular event in a patient with type 2 diabetes mellitus comprising administering to the patient therapeutically effective amounts of pemafibrate and a statin, wherein: (a) the adverse cardiovascular event is selected from nonfatal ischemic stroke, hospitalization for unstable angina requiring unplanned coronary revascularization, and cardiovascular death and the method prevents the cardiovascular event; (b) the statin is selected from moderate to high intensity statin therapy, or non-moderate to high intensity statin therapy if the patient has an LDL-C concentration ≤70 mg/dL; (c) the patient has an HDL-C concentration ≤40 mg/dL; and (d) the patient has a fasting TG concentration ≥200 mg/dL and <500 mg/dL.

In a fifth principal embodiment the invention provides a method of preventing an adverse cardiovascular event in a patient with type 2 diabetes mellitus without systemic atherosclerosis or cardiovascular disease comprising administering to the patient therapeutically effective amounts of pemafibrate and a statin, wherein: (a) the adverse cardiovascular event is selected from nonfatal ischemic stroke, hospitalization for unstable angina requiring unplanned coronary revascularization, and cardiovascular death and the method prevents the cardiovascular event; (b) the statin is selected from moderate to high intensity statin therapy, or non-moderate to high intensity statin therapy if the patient has an LDL-C concentration ≤70 mg/dL; (c) the patient has an HDL-C concentration ≤40 mg/dL; and (d) the patient has a fasting TG concentration ≥200 mg/dL and <500 mg/dL.

In a sixth principal embodiment the invention provides a method of preventing an adverse cardiovascular event in a patient with type 2 diabetes mellitus, comprising administering to the patient a therapeutically effective amount of pemafibrate, wherein the patient has: (a) an HDL-C concentration ≤40 mg/dL; (b) a fasting TG concentration ≥200 mg/dL and <500 mg/dL; (c) controlled LDL concentrations, as defined by: (i) concurrent moderate to high intensity statin therapy; (ii) an LDL-C concentration ≤70 mg/dL; or (iii) statin-intolerance and a LDL-C concentration ≤100 mg/dL; and (d) a risk factor selected from: (a) an age ≥18 years with systemic atherosclerosis; and (b) an age ≥50 years if male or ≥55 years if female, without systemic atherosclerosis.

The invention is also directed at the patient population described in a phase III clinical trial (the "PROMINENT" trial) being conducted under an Investigational New Drug Application at the United States Food and Drug Administration ("FDA"), and the treatments prescribed in that trial. Thus, in a seventh principal embodiment the invention provides a seventh principal embodiment the invention provides a method of preventing an adverse cardiovascular event selected from nonfatal myocardial infarction, nonfatal ischemic stroke, hospitalization for unstable angina requiring unplanned coronary revascularization, or cardiovascular death, in a patient in need thereof, comprising administering to the patient 0.2 mg pemafibrate twice daily for a therapeutically effective period of time, wherein the patient has: (a) type 2 diabetes mellitus defined by: (i) a hemoglobin A1c level of 6.5% or greater; (ii) a plasma glucose level ≥126 mg/dL when fasting; (iii) a plasma glucose level ≥200 mg/dL at 2 hours during oral glucose tolerance testing; (iv) a plasma glucose level ≥200 mg/dL with classic type 2 diabetes mellitus symptoms; or (v) currently receiving medication for the treatment of diabetes; (b) an HDL-C concentration ≤40 mg/dL; (c) a fasting TG concentration ≥200 mg/dL and <500 mg/dL; (d) controlled LDL concentrations, as defined by: (i) concurrent moderate to high intensity statin therapy selected from atorvastatin ≥40 mg/day (based on the weight of the free base), rosuvastatin ≥20 mg/day (based on the weight of the calcium salt), simvastatin ≥40 mg/day (based on the weight of the free base), or pitavastatin ≥4 mg/d (based on the weight of the free base), or a pharmaceutically acceptable salt thereof; (ii) a LDL-C concentration ≤70 mg/dL; or (iii) statin-intolerance and a LDL-C concentration ≤100 mg/dL; and (e) one of the following conditions: (i) an age ≥18 years with systemic atherosclerosis; or (ii) an age ≥50 years if male or ≥55 years if female, without systemic atherosclerosis; wherein: said systemic atherosclerosis is defined as (i) prior myocardial infarction or ischemic (non-hemorrhagic) stroke; (ii) coronary angiographic lesion of ≥60% stenosis in a major epicardial vessel or ≥50% left main stenosis; (iii) asymptomatic carotid disease with ≥70% carotid artery stenosis; (iv) symptomatic carotid disease with ≥50% carotid artery stenosis; (v) symptomatic lower extremity peripheral artery disease selected from intermittent claudication, rest pain, lower extremity ischemic ulceration, or major amputation with an ankle-brachial index ≤0.9 or other diagnostic testing (e.g., toe-brachial index, angiogram, or other imaging study); (vi) prior arterial revascularization procedure selected from coronary, carotid or peripheral angioplasty, stenting, bypass, atherectomy, or endarterectomy; or (vii) a combination thereof, and said method prevents the occurrence of said nonfatal myocardial infarction, nonfatal ischemic stroke, hospitalization for unstable angina requiring unplanned coronary revascularization, or cardiovascular death.

In an eighth principal embodiment the invention provides a method of treating cardiovascular disease or preventing adverse cardiovascular events in a patient with type 2 diabetes mellitus, comprising administering to the patient a therapeutically effective amount of pemafibrate or a pharmaceutically acceptable salt thereof, wherein the patient has: (a) a fasting TG concentration ≥200 mg/dL and <500 mg/dL; (b) an HDL-C concentration ≤40 mg/dL; and (c) controlled LDL-C levels.

In a ninth principal embodiment the invention provides a method of preventing the occurrence of cardiovascular events in a patient with one or more risk factors, comprising administering to the patient a therapeutically effective amount of pemafibrate or a pharmaceutically acceptable salt thereof.

Other principal embodiments relate to the use of pemafibrate to lower various markers of dyslipidemia in type 2 diabetes patients, including VLDL-C, elevated triglycerides, Apo CIII, non-HDL-C, and remnant cholesterol. Thus, in a tenth principal embodiment the invention provides a method of lowering fasting triglycerides, Apo-CIII, non-HDL-C, and remnant cholesterol in a patient with type 2 diabetes mellitus comprising administering to the patient therapeutically effective amounts of pemafibrate and a statin, wherein: (a) the statin is selected from moderate to high intensity statin therapy, or non-moderate to high intensity statin therapy if the patient has an LDL-C concentration ≤70 mg/dL; (b) the patient has an HDL-C concentration ≤40 mg/dL; (c) the patient has a fasting TG concentration ≥200 mg/dL and <500 mg/dL; and (d) the method lowers said fasting triglycerides, Apo-CIII, non-HDL-C, and remnant cholesterol.

In an eleventh principal embodiment the invention provides a method of lowering VLDL-C, remnant cholesterol, ApoCIII, and non-HDL-C in a patient with type 2 diabetes mellitus comprising administering to the patient therapeutically effective amounts of pemafibrate and a statin, wherein: (a) the statin is selected from moderate to high intensity statin therapy, or non-moderate to high intensity statin therapy if the patient has an LDL-C concentration ≤70 mg/dL; (b) the patient has an HDL-C concentration ≤40 mg/dL; (c) the patient has a fasting TG concentration ≥200 mg/dL and <500 mg/dL; and the method lowers said VLDL-C, remnant cholesterol, ApoCIII, and non-HDL-C.

Additional advantages of the invention are set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description serve to explain the invention.

FIGS. 1A-1D report changes from baseline to Week 12 in TG [A], non-HDL-C [B], Apo CIII [C] and remnant-C [D] with pemafibrate versus placebo in dyslipidemia patients receiving statin treatment, as described in Example 1. Each graph reports left to right 0.05 mg BID, 0.1 mg BID, 0.2 mg BID, 0.1 mg QD, 0.2 mg QD, and 0.4 mg QD pemafibrate.

FIGS. 2A-2D report changes from baseline to Week 12 in TG [A], non-HDL-C [B], Apo CIII [C] and remnant-C [D] with pemafibrate versus placebo in dyslipidemia patients with type 2 diabetes mellitus receiving statin treatment, as described in Example 2. Each graph reports left to right 0.05 mg BID, 0.1 mg BID, 0.2 mg BID, 0.1 mg QD, 0.2 mg QD, and 0.4 mg QD pemafibrate.

DETAILED DESCRIPTION OF THE INVENTION

Definitions and Use of Terms

Figure 1A:
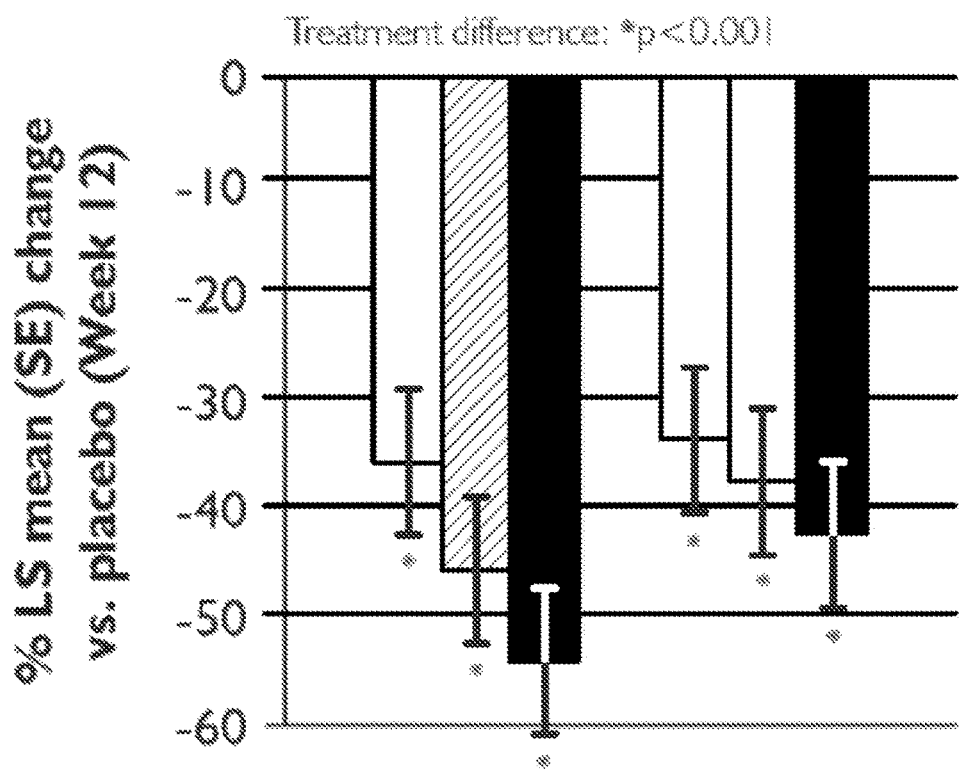
Figure 3A:
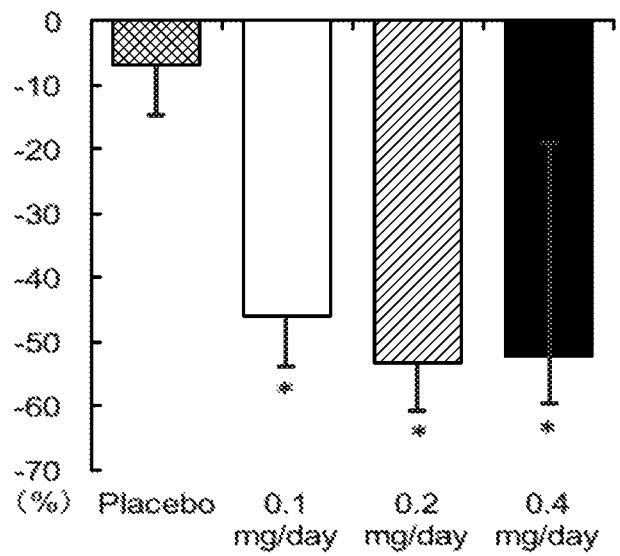
FIGS. 3A-3D report changes from baseline to Week 12 in TG [A], VLDL-C, RemL-C, Apo CIII, non-HDL-C, LDL-C and Apo B [B], HDL-C, Apo AI and Apo AII [C], and fasting plasma glucose and HOMA-IR [D], with pemafibrate versus placebo in dyslipidemia patients receiving a stable dose of pitavastatin, as reported in Example 3. Each graph reports left to right placebo, 0.1 mg BID, 0.2 mg BID, and 0.4 mg BID pemafibrate.
Figure 3B:
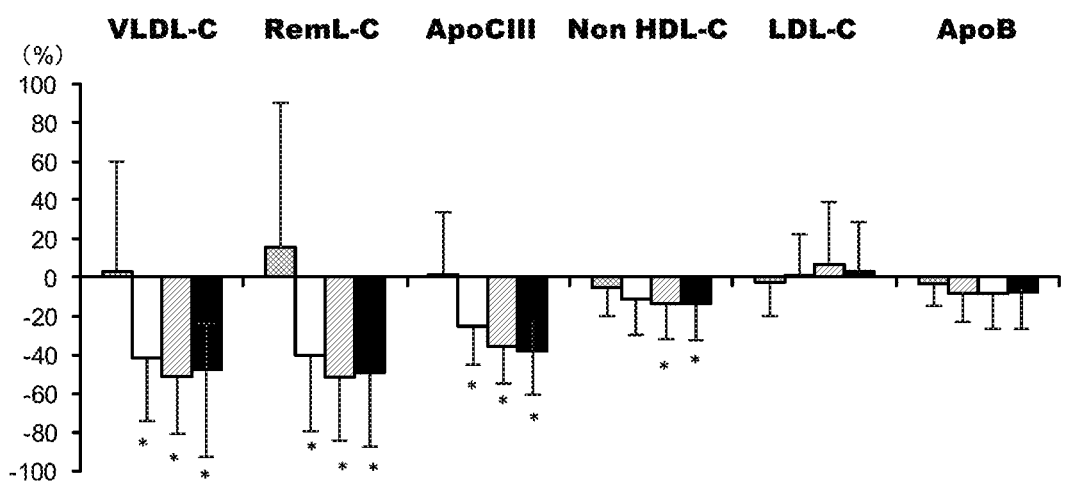
Figure 3C:
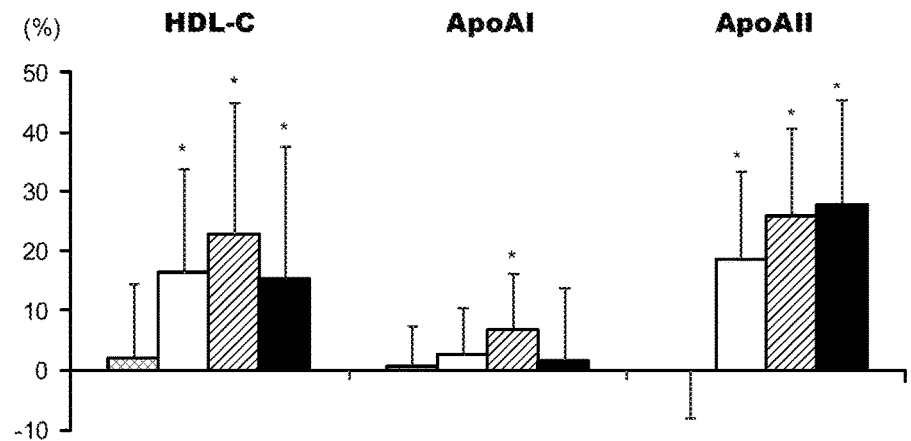
Figure 3D:
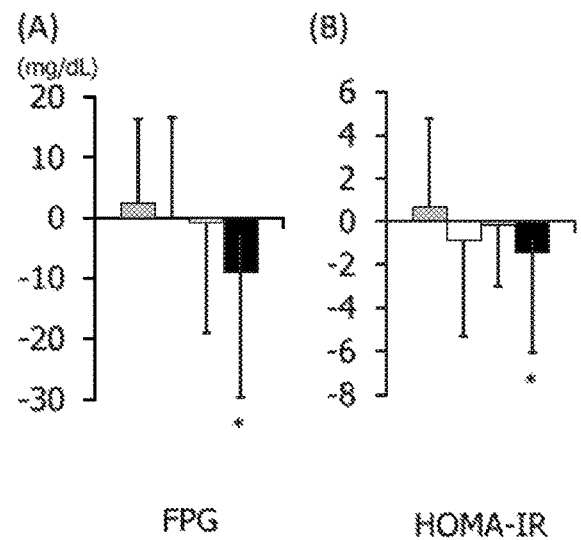

As used in the specification and claims, the singular forms "a," "an," and "the" include plural references unless the context clearly dictates otherwise. For example, the term "a pharmaceutical excipient" refers to one or more pharmaceutical excipients for use in the presently disclosed formulations and methods.

As used in this specification and in the claims which follow, the word "comprise" and variations of the word, such as "comprising" and "comprises," means "including but not limited to," and is not intended to exclude, for example, other additives, components, integers or steps. When an element is described as comprising a plurality of components, steps or conditions, it will be understood that the element can also be described as comprising any combination of such plurality, or "consisting of" or "consisting essentially of" the plurality or combination of components, steps or conditions.

The use of numerical values in the various quantitative values specified in this application, unless expressly indicated otherwise, are stated as approximations as though the minimum and maximum values within the stated ranges were both preceded by the word "about". Also, the disclosure of ranges is intended as a continuous range including every value between the minimum and maximum values recited as well as any ranges that can be formed by such values. Also, disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

As used herein, "cardiovascular events" includes any adverse cardiovascular event including cardiovascular death; nonfatal myocardial infarction; nonfatal ischemic stroke; unstable angina (e.g., unstable angina determined to be caused by myocardial ischemia by, for example, invasive or non-invasive testing, and requiring hospitalization); cardiac arrest; peripheral cardiovascular disease requiring intervention, angioplasty, bypass surgery or aneurysm repair; and onset of new congestive heart failure.

As used herein, "preventing the occurrence of a cardiovascular event" includes reducing the risk of a cardiovascular event, delaying the incidence or occurrence of a cardiovascular event, and minimizing the severity of cardiovascular event. It also refers to a time interval beginning at (a) an initial administration of a therapeutically effective amount of pemafibrate or a pharmaceutically acceptable salt thereof as disclosed herein to the patient to (b) a cardiovascular event in the patient greater than or substantially greater than a control time interval beginning at (a') initial administration of a placebo to control subjects to (b') a cardiovascular event in the control subjects.

As used herein, "therapeutically effective amount" refers to an amount sufficient to elicit the desired biological response in a patient. The therapeutically effective amount or dose depends on the age, sex and weight of the patient, and the current medical condition of the patient. The skilled artisan can determine appropriate amount or dose depending on the above factors based on his or her knowledge and the teachings contained herein.

When a drug is recited herein it will be understood that the drug can be present as either the free base of the drug or a pharmaceutically acceptable salt thereof unless the free base or a salt is specifically recited. Sometimes the dose of a drug will be based on the weight of the free base, in which case the dose will include equimolar doses of salts of the drug. Sometimes the dose will be expressed as based on the weight of a particular salt. For example, the dose of rosuvastatin can be based on the weight of the calcium salt. When the dose is expressed in this manner, and the rosuvastatin itself is not limited to the free base or any particular salt thereof, the dose of the free base or another salt can be calculated based on the molar equivalent of the recited dose of the calcium salt.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. "Pharmaceutically acceptable salts" means salts that are pharmaceutically acceptable, as defined above, and which possess the desired pharmacological activity.

The terms "treating" and "treatment," when used herein, refer to the medical management of a patient with the intent to cure, ameliorate, stabilize, or prevent a disease, pathological condition, or disorder (collectively "disorder"). These terms include active treatment, that is, treatment directed specifically toward the improvement of a disorder, and also include causal treatment, that is, treatment directed toward removal of the cause of the associated disorder. In addition, this term includes palliative treatment, that is, treatment designed for the relief of symptoms rather than the curing of the disorder; preventative treatment, that is, treatment directed to minimizing or partially or completely inhibiting or delaying the development of the disorder; and supportive treatment, that is, treatment employed to supplement another specific therapy directed toward the improvement of the disorder.

Dyslipidemia is an elevation of plasma cholesterol, triglycerides (TGs), or both, or a low high-density lipoprotein level that contributes to the development of systemic atherosclerosis. Causes may be primary (genetic) or secondary. Diagnosis is performed by measuring plasma levels of total cholesterol, TGs, and individual lipoproteins. Treatment involves dietary changes, exercise, and lipid-lowering drugs.

"Treatment of dyslipidemia" includes the correction of one or more lipid imbalances in the human body, even if the concentration of other lipids remains in an unhealthy state.

All analyte measurements recited herein, when used to define a patient described herein, are measured at the beginning of pemafibrate treatment.

Unless stated herein to the contrary, all analyte measurements are taken in the fasting state, and are based on the concentration of the analyte in plasma or serum. The fasting state means that the patient has not eaten anything in from 8 to 12 hours, except for water. Standard methods of measuring analytes can be found in Lab Protocols for NHANES 2003-2004 data published by the United States Centers for Disease Control.

Unless stated herein to the contrary, all methods described herein are performed in all ages, but they are preferably performed in adults at risk for a cardiovascular event, such as adults greater than 50 years if male and greater than 55 years if female.

As used herein, the term "significantly" refers to a level of statistical significance. The level of statistical significant can be, for example, of at least $p<0.05$, of at least $p<0.01$, of at least $p<0.005$, or of at least $p<0.001$. Whenever a numeric value or endpoint is specified herein, it will be understood in a preferred embodiment to have a degree of statistical significance of at least $p<0.05$.

Statins, also known as HMG-CoA reductase inhibitors, include atorvastatin, simvastatin, fluvastatin, pitavastatin, rosuvastatin, pravastatin, and lovastatin and their pharmaceutically acceptable salts. Statins are generally classified as high, moderate or low intensity, based on the degree of LDL-C reduction they have demonstrated in controlled clinical trials, as summarized in the following table derived from *ACC/AHA Release Updated Guideline on the Treatment of Blood Cholesterol to Reduce ASCVD Risk*, AMERICAN FAMILY PHYSICIAN, Volume 90, Number 4 (Aug. 15, 2014):

| High intensity | Moderate intensity | Low intensity |
|---|---|---|
| Daily dosage lowers LDL-C by approximately ≥50% on average Atorvastatin, 40 to 80 mg Rosuvastatin, 20 (40) mg | Daily dosage lowers LDL-C by approximately 30% to 50% on average Atorvastatin, 10 (20) mg Rosuvastatin, (5) 10 mg Simvastatin, 20 to 40 mg Pravastatin, 40 (80) mg Lovastatin, 40 mg Fluvastatini XL, 80 mg Fluvastatin, 40 mg twice daily Pitavastatin, 2 to 4 mg | Daily dosage lowers LDL-C by <30% average Simvastatin, 10 mg Pravastatin, 10 to 20 mg Lovastatin, 20 mg Fluvastatin, 20 to 40 mg Pitavastatin, 1 mg |

Note:
Specific statins and dosages noted in bold were evaluated in RCTs included in critical question 1, critical question 2, and the Cholesteral Treatment Trialists 2010 meta-analysis included in critical question 3 (see full guideline for details). All of these RCTs demonstrated a reduction in major cardiovascular events.
Statins and dosages listed in italics are approved by the U.S. Food and Drug Administration but were not tested in the RCTs reviewed.
RCT = randomized controlled trial.

When the term "moderate to high intensity statin therapy" is employed, the following group of statin therapies is preferably administered, and can be substituted for the term "moderate to high intensity statin therapy": atorvastatin ≥40 mg/day (based on the weight of the free base), rosuvastatin ≥20 mg/day (based on the weight of the calcium salt), and simvastatin ≥40 mg/day (based on the weight of the free base), or pitavastatin ≥4 mg/day. The term "non-moderate to high intensity statin therapy" refers to any statin therapy other than atorvastatin ≥40 mg/day (based on the weight of the free base), rosuvastatin ≥20 mg/day (based on the weight of the calcium salt), and simvastatin ≥40 mg/day (based on the weight of the free base), or pitavastatin ≥4 mg/day.

Discussion of Principal Embodiments

The invention is described herein in terms of principal embodiments and subembodiments. It will be understood that each of the subembodiments can modify any of the principal embodiments, unless such modification is logically inconsistent or expressly disallowed in this document. It will be further understood that the principal embodiments can be combined in any manner, and that the subembodiments can be combined in any manner to further modify any of the principal embodiments, unless such combination is logically inconsistent or expressly disallowed in this document.

In a first principal embodiment the invention provides a method of preventing an adverse cardiovascular event in a patient with type 2 diabetes mellitus comprising administering to the patient therapeutically effective amounts of pemafibrate and a statin, wherein: (a) the statin is selected from moderate to high intensity statin therapy, or non-moderate to high intensity statin therapy if the patient has an LDL-C concentration ≤70 mg/dL; (b) the patient has an HDL-C concentration ≤40 mg/dL; and (c) the patient has a fasting TG concentration ≥200 mg/dL and <500 mg/dL; and the method prevents the cardiovascular event.

In a second principal embodiment the invention provides a method of preventing an adverse cardiovascular event in a patient with type 2 diabetes mellitus without systemic atherosclerosis or cardiovascular disease comprising administering to the patient therapeutically effective amounts of pemafibrate and a statin, wherein: (a) the statin is selected from moderate to high intensity statin therapy, or non-moderate to high intensity statin therapy if the patient has an LDL-C concentration ≤70 mg/dL; (b) the patient has an HDL-C concentration ≤40 mg/dL; (c) the patient has a fasting TG concentration ≥200 mg/dL and <500 mg/dL; and (d) the method prevents the cardiovascular event.

In a third principal embodiment the invention provides a method of preventing an adverse cardiovascular event in a patient with type 2 diabetes mellitus and a HbA1c concentration greater than 8.1% comprising administering to the patient therapeutically effective amounts of pemafibrate and a statin, wherein: (a) the statin is selected from moderate to high intensity statin therapy, or non-moderate to high intensity statin therapy if the patient has an LDL-C concentration ≤70 mg/dL; (b) the patient has an HDL-C concentration ≤40 mg/dL; (c) the patient has a fasting TG concentration ≥200 mg/dL and <500 mg/dL; and (d) the method prevents the cardiovascular event.

In a fourth principal embodiment the invention provides a method of preventing an adverse cardiovascular event in a patient with type 2 diabetes mellitus comprising administering to the patient therapeutically effective amounts of pemafibrate and a statin, wherein: (a) the adverse cardiovascular event is selected from nonfatal ischemic stroke, hospitalization for unstable angina requiring unplanned coronary revascularization, and cardiovascular death and the method prevents the cardiovascular event; (b) the statin is selected from moderate to high intensity statin therapy, or non-moderate to high intensity statin therapy if the patient has an LDL-C concentration ≤70 mg/dL; (c) the patient has an HDL-C concentration ≤40 mg/dL; and (d) the patient has a fasting TG concentration ≥200 mg/dL and <500 mg/dL.

In a fifth principal embodiment the invention provides a method of preventing an adverse cardiovascular event in a patient with type 2 diabetes mellitus without systemic atherosclerosis or cardiovascular disease comprising administering to the patient therapeutically effective amounts of pemafibrate and a statin, wherein: (a) the adverse cardiovascular event is selected from nonfatal ischemic stroke, hospitalization for unstable angina requiring unplanned coronary revascularization, and cardiovascular death and the method prevents the cardiovascular event; (b) the statin is selected from moderate to high intensity statin therapy, or non-moderate to high intensity statin therapy if the patient has an LDL-C concentration ≤70 mg/dL; (c) the patient has an HDL-C concentration ≤40 mg/dL; and (d) the patient has a fasting TG concentration ≥200 mg/dL and <500 mg/dL.

In a sixth principal embodiment the invention provides a method of preventing an adverse cardiovascular event in a patient with type 2 diabetes mellitus, comprising administering to the patient a therapeutically effective amount of pemafibrate, wherein the patient has: (a) an HDL-C concentration ≤40 mg/dL; (b) a fasting TG concentration ≥200 mg/dL and <500 mg/dL; (c) controlled LDL concentrations, as defined by: (i) concurrent moderate to high intensity statin therapy; (ii) a LDL-C concentration ≤70 mg/dL; or (iii) statin-intolerance and a LDL-C concentration ≤100 mg/dL; and (d) a risk factor selected from: (a) an age ≥18 years with systemic atherosclerosis; and (b) an age ≥50 years if male or ≥55 years if female, without systemic atherosclerosis.

In a seventh principal embodiment the invention provides a method of preventing an adverse cardiovascular event selected from nonfatal myocardial infarction, nonfatal ischemic stroke, hospitalization for unstable angina requiring unplanned coronary revascularization, or cardiovascular death, in a patient in need thereof, comprising administering to the patient 0.2 mg pemafibrate twice daily for a therapeutically effective period of time, wherein the patient has: (a) type 2 diabetes mellitus defined by: (i) a hemoglobin A1c level of 6.5% or greater; (ii) a plasma glucose level ≥126 mg/dL when fasting; (iii) a plasma glucose level ≥200 mg/dL at 2 hours during oral glucose tolerance testing; (iv) a plasma glucose level ≥200 mg/dL with classic type 2 diabetes mellitus symptoms; or (v) currently receiving medication for the treatment of diabetes; (b) an HDL-C concentration ≤40 mg/dL; (c) a fasting TG concentration ≥200 mg/dL and <500 mg/dL; (d) controlled LDL concentrations, as defined by: (i) concurrent moderate to high intensity statin therapy selected from atorvastatin ≥40 mg/day (based on the weight of the free base), rosuvastatin ≥20 mg/day (based on the weight of the calcium salt), simvastatin ≥40 mg/day (based on the weight of the free base), or pitavastatin ≥4 mg/d (based on the weight of the free base), or a pharmaceutically acceptable salt thereof; (ii) a LDL-C concentration ≤70 mg/dL; or (iii) statin-intolerance and a LDL-C concentration ≤100 mg/dL; and (e) one of the following conditions: (i) an age ≥18 years with systemic atherosclerosis; or (ii) an age ≥50 years if male or ≥55 years if female, without systemic atherosclerosis; wherein: said systemic atherosclerosis is defined as (i) prior myocardial infarction or ischemic (non-hemorrhagic) stroke; (ii) coronary angiographic lesion of ≥60% stenosis in a major epicardial vessel or ≥50% left main stenosis; (iii) asymptomatic carotid disease with ≥70% carotid artery stenosis; (iv) symptomatic carotid disease with ≥50% carotid artery stenosis; (v) symptomatic lower extremity peripheral artery disease selected from intermittent claudication, rest pain, lower extremity ischemic ulceration, or major amputation with an ankle-brachial index ≤0.9 or other diagnostic testing (e.g., toe-brachial index, angiogram, or other imaging study); (vi) prior arterial revascularization procedure selected from coronary, carotid or peripheral angioplasty, stenting, bypass, atherectomy, or endarterectomy; or (vii) a combination thereof, and said method prevents the occurrence of said nonfatal myocardial infarction, nonfatal ischemic stroke, hospitalization for unstable angina requiring unplanned coronary revascularization, or cardiovascular death.

In an eighth principal embodiment the invention provides a method of treating cardiovascular disease or preventing adverse cardiovascular events in a patient with type 2 diabetes mellitus, comprising administering to the patient a therapeutically effective amount of pemafibrate or a pharmaceutically acceptable salt thereof, wherein the patient has: (a) a fasting TG concentration ≥200 mg/dL and <500 mg/dL; (b) an HDL-C concentration ≤40 mg/dL; and (c) controlled LDL-C levels.

In a ninth principal embodiment the invention provides a method of preventing the occurrence of cardiovascular events in a patient with one or more risk factors, comprising administering to the patient a therapeutically effective amount of pemafibrate or a pharmaceutically acceptable salt thereof.

In a tenth principal embodiment the invention provides a method of lowering fasting triglycerides, Apo-CIII, non- HDL-C, and remnant cholesterol in a patient with type 2 diabetes mellitus comprising administering to the patient therapeutically effective amounts of pemafibrate and a statin, wherein: (a) the statin is selected from moderate to high intensity statin therapy, or non-moderate to high intensity statin therapy if the patient has an LDL-C concentration ≤70 mg/dL; (b) the patient has an HDL-C concentration ≤40 mg/dL; (c) the patient has a fasting TG concentration ≥200 mg/dL and <500 mg/dL; and (d) the method lowers said fasting triglycerides, Apo-CIII, non-HDL-C, and remnant cholesterol.

In an eleventh principal embodiment the invention provides a method of lowering VLDL-C, remnant cholesterol, ApoCIII, and non-HDL-C in a patient with type 2 diabetes mellitus comprising administering to the patient therapeutically effective amounts of pemafibrate and a statin, wherein: (a) the statin is selected from moderate to high intensity statin therapy, or non-moderate to high intensity statin therapy if the patient has an LDL-C concentration ≤70 mg/dL; (b) the patient has an HDL-C concentration ≤40 mg/dL; (c) the patient has a fasting TG concentration ≥200 mg/dL and <500 mg/dL; and the method lowers said VLDL-C, remnant cholesterol, ApoCIII, and non-HDL-C.

Discussion of Subembodiments

Each of the following subembodiments can apply to limit each and every one of the foregoing principal embodiment, although it will be understood that the subembodiment will not apply if it is already wholly subsumed by the principal embodiment. It will also be understood that the subembodiments and can be combined with each other in any manner that is logically and mathematically possible, adopting the more restrictive value when two values for the same limitation are expressed, to define further subembodiments.

Any of the principal embodiments can be practiced in patients with type 2 diabetes, which in turn can be defined in a variety of ways. In one subembodiment the type 2 diabetes mellitus is defined by a hemoglobin A1c level of 6.5% or greater, or even 8.1% or greater. In other subembodiments the type 2 diabetes mellitus is defined by a plasma glucose level ≥126 mg/dL when fasting, a plasma glucose level ≥126 mg/dL and <175 mg/dL or <165 mg/dL when fasting, a plasma glucose level ≥200 mg/dL at 2 hours during oral glucose tolerance testing, or a plasma glucose level ≥200 mg/dL with classic type 2 diabetes mellitus symptoms, or currently receiving medication for the treatment of type 2 diabetes mellitus. In one particular subembodiment the type 2 diabetes mellitus is defined by a hemoglobin A1c level of 6.5% or greater, and a plasma glucose level: (a) ≥126 mg/dL when fasting; (b) ≥200 mg/dL at 2 hours during oral glucose tolerance testing; or (c) ≥200 mg/dL with classic type 2 diabetes mellitus symptoms.

The method can also be practiced with various moderate to high intensity statin regimens. In various subembodiments, the moderate to high intensity statin therapy is atorvastatin ≥40 mg/day (based on the weight of the free base), rosuvastatin ≥20 mg/day (based on the weight of the calcium salt), and simvastatin ≥40 mg/day (based on the weight of the free base), or pitavastatin ≥4 mg/day. In another subembodiment, the moderate to high intensity statin therapy is atorvastatin ≥40 mg/day (based on the weight of the free base), rosuvastatin ≥20 mg/day (based on the weight of the calcium salt), or simvastatin ≥40 mg/day (based on the weight of the free base).

Alternatively, the method can be practiced with any statin therapy other than the foregoing moderate to high intensity therapies, particularly when LDL-C levels are well-controlled. Thus, in another subembodiment non-moderate to high intensity statin therapy is administered to the patient, and the patient has an LDL-C concentration ≤70 mg/dL. In another distinct subembodiment, the patient is on any statin therapy.

In one particular subembodiment, the patient has been on unchanged statin therapy for 12 weeks prior to commencing said pemafibrate administration. In another particular subembodiment the patient remains on unchanged statin therapy for a therapeutically effective period of time. A patient on >40 mg/simvastatin per day has preferably been on this dose for 12 months prior to commencing said pemafibrate administration.

Any of the methods can also be practiced based solely on the LDL-C status of the patient. Therefore, in various subembodiments the patient has an LDL-C concentration ≤70 mg/dL, ≤60 mg/dL, or ≤50 mg/dL.

The methods can also be practiced in primary prevention or secondary prevention. Thus, in one subembodiment the patient has systemic atherosclerosis. In another subembodiment the patient has cardiovascular disease. In another subembodiment the patient does not have systemic atherosclerosis. In yet another subembodiment the patient does not have cardiovascular disease. In one particular subembodiment the patient has an age ≥18 years with systemic atherosclerosis. In another particular subembodiment the patient has an age ≥18 years and <40 years with systemic atherosclerosis. In still another subembodiment the patient has an age ≥50 years if male or ≥55 years if female, without systemic atherosclerosis.

Systemic atherosclerosis can be defined in various manners. In one subembodiment the systemic atherosclerosis is defined as prior myocardial infarction or ischemic (non-hemorrhagic) stroke. In another subembodiment the systemic atherosclerosis is defined as coronary angiographic lesion of ≥60% stenosis in a major epicardial vessel or ≥50% left main stenosis. In another subembodiment the systemic atherosclerosis is defined as asymptomatic carotid disease with ≥70% carotid artery stenosis. In still another subembodiment the systemic atherosclerosis is defined as symptomatic carotid disease with ≥50% carotid artery stenosis. In still another subembodiment the systemic atherosclerosis is defined as symptomatic lower extremity peripheral artery disease selected from intermittent claudication, rest pain, lower extremity ischemic ulceration, or major amputation with an ankle brachial index ≤0.9 or other diagnostic testing (e.g., toe-brachial index, angiogram, or other imaging study). In yet another subembodiment the systemic atherosclerosis is defined as prior arterial revascularization procedure selected from coronary, carotid or peripheral angioplasty, stenting, bypass, atherectomy, or endarterectomy. In one subembodiment, systemic atherosclerosis is defined by one or any combination of the foregoing criteria.

One particular advantage of the therapy is it is targeted at cardiovascular events not traditionally affected by fibrates. Thus, in one subembodiment the therapy is targeted at non-fatal myocardial infarction, ischemic stroke, hospitalization for unstable angina requiring unplanned coronary revascularization, and cardiovascular death, particularly when the patient is at risk for any of the foregoing conditions. In various particular subembodiments, the patient is at risk for an ischemic stroke, and the method prevents ischemic stroke; the patient is at risk for hospitalization for unstable angina requiring unplanned coronary revascularization and the method prevents said hospitalization; or the patient is at risk for cardiovascular death and the method prevents said cardiovascular death.

The methods of the present invention can also be practiced in patients with differing levels of HDL-C. Thus, in various subembodiments the patient has an HDL-C concentration less than 40 mg/dL, 35 mg/dL, or even 30 mg/dL. In one subembodiment the patient has an HDL-C ranging from 35 to 40 mg/dL.

The methods can also be practiced with the administration of other therapeutic agents. Thus, for example, in one subembodiment the method further comprises administering lipid lowering therapy selected from ezetimibe, probucol, niacin, cholestyramine, eicosapentaenoic acid (EPA) and docosahexaenoic acid (DHA), and combinations thereof. In another subembodiment the method further comprises administering a cardiovascular drug selected from angiotensin-converting-enzyme inhibitors, angiotensin-receptor blockers, aspirin, beta-blockers, nitrates, and thiazide diuretics. In another embodiment the pemafibrate/statin combination is administered with ezetimibe and/or a proprotein convertase subtilisin/kexin type 9 (PCSK9) inhibitor.

In one particular subembodiment the method is practiced in combination with a diabetes medication. Preferred diabetes medications are selected from alpha-glucosidase inhibitors selected from acarbose and miglitol, a biguanide such as metformin, a dopamine agonist such as bromocriptine, a DPP-4 inhibitor selected from alogliptin, linagliptin, saxagliptin, and sitagliptin, a glucagon-like peptide selected from albiglutide, dulaglutide, exenatide, and liraglutide, a meglitinide selected from nateglinide and repaglinide, a sodium glucose transporter (SGLT) 2 inhibitor selected from dapagliflozin, canagliflozin, and empagliflozin, a sulfonylurea selected from glimepiride, gliclazide, glipizide, glyburide, chlorpropamide, tolazamide, and tolbutamide, a thiazolidinedione selected from rosiglitazone and pioglitazone, and combinations thereof.

In one particular subembodiment the method is practiced along with aggressive glycemic control to a type 2 diabetes patient. More particularly, the method is practiced by co-administering a diabetes medication targeting a HbA1c concentration of less than 6%.

The method can also be defined based on its effect on biochemical markers, or other biomarkers can be used to characterize the patient being treated. Thus, in one subembodiment the method lowers fasting triglycerides, Apo-CIII, non-HDL-C, and remnant cholesterol. In another subembodiment the method lowers VLDL-C, remnant cholesterol, Apo-CIII, and non-HDL-C. In another subembodiment the method lowers fasting plasma glucose and insulin resistance. In yet another subembodiment the method lowers fasting triglycerides, Apo-CIII, non-HDL-C, and remnant cholesterol more in diabetic patients than non-diabetic patients. In still another subembodiment the patient's non-HDL-C concentration is greater than 130 mg/dL, remnant cholesterol level is greater than 5.0 mg/dL, and Apo CIII concentration is from 5.8 to 10 mg/dL for male and 5.4 to 9.0 mg/dL for female.

The method is preferably practiced for a therapeutically effective period of time for optimal benefit. In various subembodiments, the therapeutically effective period of time is 3 years, 4, years, 5 years, 6 years, or even 10 or 15 years.

The therapeutically effective dose of pemafibrate in one subembodiment is from 0.2 to 1.0 mg administered orally per day based on the weight of the free base. In another subembodiment the therapeutically effective amount of pemafibrate is 0.4 mg administered orally per day based on the weight of the free base. In still another subembodiment the therapeutically effective amount of pemafibrate is 0.4 mg/day administered orally in divided daily doses based on the weight of the free base.

The method also has safety benefits over other fibrate therapies that allow its use in different patient populations. Thus, in one subembodiment the patient is at risk for rhabdomyolysis, preferably as shown by elevated creatinine kinase. In another subembodiment the patient has renal insufficiency or renal failure.

Additional Embodiments

The present invention further provides the following:
1) A method of preventing the occurrence of cardiovascular events in a patient with one or more risk factors, comprising administering to the patient a therapeutically effective amount of pemafibrate or a pharmaceutically acceptable salt thereof.
2) The method according to 1), wherein the patient has type 2 diabetes mellitus.
3) The method according to 1), wherein the patient has an age greater than or equal to 50 years if male or 55 years if female, or systemic atherosclerosis.
4) The method according to 1), wherein the patient is taking concurrent statins.
5) The method according to 1), wherein the patient has a fasting TG concentration ≥200 mg/dL and <500 mg/dL.
6) The method according to 1), wherein the patient has an HDL-C concentration ≤40 mg/dL.
7) The method according to 1), wherein the patient has:
   a) type 2 diabetes mellitus;
   b) a fasting TG concentration ≥200 mg/dL and <500 mg/dL; and
   c) an HDL-C concentration ≤40 mg/dL.
8) The method according to 7) wherein:
   a) the patient has an age greater than or equal to 50 years if male or 55 years if female, or systemic atherosclerosis;
   b) the therapeutically effective amount of pemafibrate or pharmaceutically acceptable salt thereof is 0.4 mg, administered orally per day; and
   c) the cardiovascular events are selected from nonfatal myocardial infarction, nonfatal ischemic stroke, hospitalization for unstable angina requiring unplanned coronary revascularization, cardiovascular death, or a combination thereof.
9) The method according to 1), wherein the patient is:
   a) on concomitant moderate to high intensity statin therapy;
   b) on concomitant lipid-lowering therapy other than the concomitant moderate to high intensity statin therapy and has an LDL-C concentration ≤70 mg/dL; or
   c) statin-intolerant and has an LDL-C concentration ≤100 mg/dL.
10) The method according to 1), wherein the therapeutically effective amount of pemafibrate or pharmaceutically acceptable salt thereof is from 0.2 to 1.0 mg, administered orally per day.
11) The method according to 1), wherein the therapeutically effective amount of pemafibrate or pharmaceutically acceptable salt thereof is 0.4 mg, administered orally per day.
12) The method according to 1), wherein the therapeutically effective amount of pemafibrate or pharmaceutically acceptable salt thereof is 0.2 mg, administered orally twice daily.

13) The method according to 1), wherein the cardiovascular events are selected from nonfatal myocardial infarction, nonfatal ischemic stroke, hospitalization for unstable angina requiring unplanned coronary revascularization, cardiovascular death, or a combination thereof.

14) The method according to 1), wherein the patient has type 2 diabetes mellitus as defined by:
  a) a hemoglobin A1c level of 6.5% or greater; and
  b) a plasma glucose level selected from:
    i) greater than or equal to 126 mg/dL when fasting;
    ii) greater than or equal to 200 mg/dL at 2 hours during oral glucose tolerance testing; or
    iii) greater than or equal to 200 mg/dL with classic type 2 diabetes mellitus symptoms.

15) The method according to 1), wherein the patient has cardiovascular disease.

16) A method of treating dyslipidemia in a patient with type 2 diabetes mellitus comprising administering to the patient a therapeutically effective amount of pemafibrate or a pharmaceutically acceptable salt thereof, wherein the patient has:
  a) a fasting TG concentration ≥175 mg/dL and ≤500 mg/dL; and
  b) an HDL-C concentration ≤50 mg/dL if male or ≤55 mg/dL if female.

17) The method according to 16), wherein the patient has:
  a) a fasting TG concentration ≥200 mg/dL and <500 mg/dL; and
  b) an HDL-C concentration <40 mg/dL.

18) The method according to 16), wherein the therapeutically effective amount of pemafibrate or pharmaceutically acceptable salt thereof is from 0.1 to 1.0 mg, administered orally per day.

19) The method according to 16), wherein the therapeutically effective amount of pemafibrate or pharmaceutically acceptable salt thereof is 0.4 mg, administered orally per day.

20) The method according to 16), wherein the therapeutically effective amount of pemafibrate or pharmaceutically acceptable salt thereof is 0.2 mg, administered orally twice daily.

21) The method according to 16), wherein the patient has type 2 diabetes mellitus as defined by:
  a) hemoglobin A1c level of 6.5% or greater; and
  b) plasma glucose level is selected from:
    i) greater than or equal to 126 mg/dL when fasting;
    ii) greater than or equal to 200 mg/dL at 2 hours during oral glucose tolerance testing; or
    iii) greater than or equal to 200 mg/dL with classic type 2 diabetes mellitus symptoms.

22) The method according to 16), wherein:
  a) the patient has an age greater than or equal to 50 years if male or 55 years if female, or systemic atherosclerosis;
  b) the therapeutically effective amount of pemafibrate or pharmaceutically acceptable salt thereof is 0.4 mg, administered orally per day; and
  c) the method is effective to prevent the occurrence of a cardiovascular event selected from nonfatal myocardial infarction, nonfatal ischemic stroke, hospitalization for unstable angina requiring unplanned coronary revascularization, cardiovascular death, or a combination thereof 23) The method according to 16) or 17), wherein the patient has an LDL-C concentration ≤100 mg/dL.

24) The method according to 16) or 17), wherein the patient is:
  a) on concomitant moderate to high intensity statin therapy;
  b) on concomitant lipid-lowering therapy other than the concomitant moderate to high intensity statin therapy and has an LDL-C concentration ≤70 mg/dL; or
  c) statin-intolerant and has an LDL-C concentration ≤100 mg/dL.

25) The method according to 16), wherein the patient has cardiovascular disease.

26) A method of treating type 2 diabetes mellitus in a patient in need thereof comprising administering to the patient a therapeutically effective amount of pemafibrate or a pharmaceutically acceptable salt thereof, wherein the patient has:
  a) a fasting TG concentration ≥200 mg/dL and <500 mg/dL;
  b) an HDL-C concentration ≤40 mg/dL; and
  c) controlled LDL-C levels.

27) A method of treating cardiovascular disease or preventing adverse cardiovascular events in a patient with type 2 diabetes mellitus, comprising administering to the patient a therapeutically effective amount of pemafibrate or a pharmaceutically acceptable salt thereof, wherein the patient has:
  a) a fasting TG concentration ≥200 mg/dL and <500 mg/dL;
  b) an HDL-C concentration ≤40 mg/dL; and
  c) controlled LDL-C levels.

28) The method according to 27) for preventing adverse cardiovascular events wherein the cardiovascular event is selected from nonfatal myocardial infarction, nonfatal ischemic stroke, hospitalization for unstable angina requiring unplanned coronary revascularization, cardiovascular death, or a combination thereof 29) A method of prolonging the time to first occurrence of:
  a) any component of the primary endpoint in a subgroup of subjects defined at baseline by: sex; presence or absence of established CVD; and baseline lipid lowering therapy as defined hierarchically by:
    i) receiving treatment with a stable dose (i.e. for at least 12 weeks) of a qualifying moderate to high intensity statin; or
    ii) statin intolerant and having evidence of LDL<100 mg/dl (2.59 mmol/L) by a local laboratory determination within the previous 12 months; or
    iii) having evidence of LDL-C<70 mg/dl (1.81 mmol/L) by a local laboratory determination within the previous 12 months if untreated or on stable dosing (i.e. for at least 12 weeks) of another lipid-lowering regimen including a PCSK9 inhibitor.
  b) any component of nonfatal MI, nonfatal ischemic stroke, hospitalization of for unstable angina requiring unplanned coronary revascularization, CV death, or any coronary revascularization;
  c) any component of nonfatal MI, nonfatal ischemic stroke, hospitalization for unstable angina requiring unplanned coronary revascularization, or all-cause mortality;
  d) any component of nonfatal MI, nonfatal ischemic stroke, CV death, any coronary revascularization, or hospitalization for heart failure;
  e) any component of nonfatal MI, nonfatal stroke (any), CV death, or hospitalization for unstable angina requiring unplanned coronary revascularization;

f) individual components of the primary endpoint, non-fatal stroke (any), all cause mortality, and hospitalization for heart failure;
g) diabetic retinopathy, as assessed by use of retinal laser treatment, anti-vascular endothelial growth factor therapy, or vitrectomy due to development of and/or deterioration in diabetic retinopathy;
h) diabetic nephropathy, as assessed by an increase in microalbumin/creatinine ratio to >30 mg/g among those without microalbuminuria at baseline, and categorical change from baseline albuminuria (normo-, micro-, or macroalbuminuria), doubling of creatinine from baseline, creatinine level >6.0 mg/dl, glomerular filtration rate (GFR)<15 ml/ml, or initiation of renal replacement therapy (dialysis or transplant), among all subjects; and
i) peripheral artery disease, defined as incidence of lower-extremity revascularization, intermittent claudication, rest pain, lower-extremity ischemic ulceration, or amputation with either ankle brachial index ≤0.9 or other diagnostic testing (e.g., angiogram, toe-brachial index, or imaging study),
wherein the method comprises administering to a subject in need thereof a therapeutically effective amount of pemafibrate or a pharmaceutically acceptable salt thereof.
30) A method of prolonging the time to first occurrence of:
a) any component of the 3-component composite endpoint of non-fatal MI, non-fatal stroke, or cardiovascular death;
b) any component of the primary endpoint or hospitalization for heart failure;
c) any component of the primary endpoint or all-cause mortality;
d) any component of the primary endpoint, any coronary revascularization, or hospitalization for heart failure; or
e) any new or worsening peripheral artery disease, defined as incidence of lower extremity revascularization, intermittent claudication, rest pain, lower extremity ischemic ulceration, or major amputation with either ankle-brachial index ≤0.9 or other diagnostic testing (e.g., toe-brachial index, angiogram, or other imaging study), wherein the method comprises administering to a subject in need thereof a therapeutically effective amount of pemafibrate or a pharmaceutically acceptable salt thereof.
31) The method according to 3), wherein systemic atherosclerosis is defined by:
a) prior myocardial infarction or ischemic (non-hemorrhagic) stroke;
b) coronary angiographic lesion of ≥60% stenosis in a major epicardial vessel or ≥50% left main stenosis;
c) asymptomatic carotid disease with ≥70% carotid artery stenosis;
d) symptomatic carotid disease with ≥50% carotid artery stenosis;
e) symptomatic lower extremity peripheral artery disease selected from intermittent claudication, rest pain, or lower extremity ischemic ulceration with an ankle-brachial index ≤0.9; or
f) prior arterial revascularization procedure selected from coronary, carotid or peripheral angioplast, stenting, bypass, atherectomy, or endarterectomy.
32) The method according to 1), wherein the patient does not have systemic atherosclerosis.
33) The method of 1), wherein the patient is taking concurrent statins and has:
a) type 2 diabetes mellitus;
b) a fasting TG concentration ≥200 mg/dL and <500 mg/dL; and
c) an HDL-C concentration ≤40 mg/dL.
34) The method of 27), wherein the patient is on concurrent statins.

These additional embodiments are discussed narratively and in additional detail below. In a first additional embodiment, the invention provides a method of preventing the occurrence of cardiovascular events in a patient with one or more risk factors, comprising administering to the patient an effective amount of pemafibrate or a pharmaceutically acceptable salt thereof.

In a preferred first additional embodiment, the invention provides a method of preventing the occurrence of cardiovascular events in a patient with one or more of multiple risk factors, comprising administering to the patient an effective amount of pemafibrate or a pharmaceutically acceptable salt thereof.

According to this embodiment, the occurrence of cardiovascular events can be prevented. That is, the occurrence of the following events can be prevented: cardiovascular death; nonfatal myocardial infarction; nonfatal ischemic stroke; coronary revascularization; unstable angina (e.g., unstable angina determined to be caused by myocardial ischemia by, for example, invasive or non-invasive testing, and requiring hospitalization); cardiac arrest; peripheral cardiovascular disease requiring intervention, angioplasty, bypass surgery or aneurysm repair; and onset of new congestive heart failure.

In a preferred first additional embodiment, the occurrence of: (a) nonfatal myocardial infarction, (b) nonfatal ischemic stroke, (c) hospitalization for unstable angina requiring unplanned coronary revascularization, (d) cardiovascular death; or a combination thereof can be prevented.

In another preferred first additional embodiment, the risk of a cardiovascular event, for example (a) nonfatal myocardial infarction, (b) nonfatal ischemic stroke, (c) hospitalization for unstable angina requiring unplanned coronary revascularization, (d) cardiovascular death; or a combination thereof can be reduced.

In another preferred first additional embodiment, the method can be performed in patients along with statin treatment, or who have controlled LDL-C levels (i.e. LDL-C levels less than or equal to 70 or 100 mg/dL). If the patient is on concomitant moderate to high intensity statin therapy, it can be assumed that the patient has low or controlled LDL-C levels. In this embodiment, statins can be selected from rosuvastatin, pitavastatin, atorvastatin, fluvastatin, simvastatin, pravastatin and lovastatin, preferably selected from atorvastatin ≥40 mg/d, rosuvastatin ≥20 mg/d, simvastatin ≥40 mg/d, or pitavastatin 4 mg/d. In addition, if the patient is on concomitant lipid-lowering therapy, the patient can be presumed to have low or controlled LDC levels if the patient has a LDL-C concentration less than or equal to 70 mg/dL. If the patient is statin-intolerant, the patient can be presumed to have low or controlled LDL levels if the patient has a LDL-C concentration less than or equal to 100 mg/dL. In this embodiment, "lipid-lowering therapy" includes therapy in which the patient is treated by a lipid-lowering drug such as a statin e.g. rosuvastatin, pitavastatin, atorvastatin, fluvastatin, simvastatin, pravastatin and lovastatin; an inhibitor of cholesterol absorption in the small intestine e.g. ezetimibe; probucol; niacin; bile acid sequestrants, e.g.

cholestyramine; omega-3 fatty acids, e.g. eicosapentaenoic acid (EPA) and docosahexaenoic acid (DHA).

Thus, in one preferred first additional embodiment the method is performed in patients: a) on concomitant moderate to high intensity statin therapy; b) on concomitant lipid-lowering therapy other than the concomitant moderate to high intensity statin therapy and having an LDL-C concentration ≤70 mg/dL; or c) who are statin-intolerant and have an LDL-C concentration ≤100 mg/dL.

This first additional embodiment is preferably practiced in patients with one or more risk factors for cardiovascular events selected from: (i) elevated fasting triglyceride levels; (ii) low HDL-C; (iii) type 2 diabetes mellitus; (iv) age (male ≥50 or female ≥55); (v) systemic atherosclerosis; (vi) hypertension; (vii) smoking; and (viii) family history of early coronary heart disease. It is known that a habit of smoking and/or a family history of early coronary heart disease raise the risk for cardiovascular events. As used herein, the risk factors for cardiovascular disease are also referred as "multiple risk factors".

Elevated fasting triglyceride levels refers to a fasting triglyceride level greater than 150, 160, 170, 175, 180, 190, 200, or 210 mg/dL triglycerides, with 200 mg/dL (2.26 mmol/L) defining a preferred cutoff value. The upper limit of the patient's fasting triglyceride is not particularly limited, but less than 500 mg/dL is a preferred cutoff value.

Low HDL-C levels refers to an HDL-C level at which the patient is at risk for a cardiovascular event, and can be different depending on the patient's sex. In preferred embodiments, the patient can be said to have a low HDL-C level if the patient has an HDL-C concentration less than 55, 50, 45, 40 or 35 mg/dL, preferably ≤50 mg/dL if male or ≤55 mg/dL if female. More preferably, 40 mg/dL (1.034 mmol/L) HDL-C will define the cutoff value.

Other lipid values and their cutoff values can also be used to define the patients treated by this first additional embodiment, including elevated non-HDL-C, elevated Apo CIII, and elevated remnant cholesterol. In one embodiment, the patient's non-HDL-C concentration is greater than 130, 160, or 190 mg/dL. In another embodiment, the patient's remnant cholesterol level is greater than 5.0, 5.3, 5.6, or 5.9 mg/dL. In yet another embodiment, the patient's Apo CIII concentration is 5 to 20 mg/dL, for example, 5.8 to 10 mg/dL for male and 5.4 to 9.0 mg/dL for female.

In another preferred first additional embodiment, the patient being treated has type 2 diabetes mellitus, defined in one embodiment as a patient with: elevated glycated hemoglobin A1c levels and/or elevated plasma glucose levels. A patient having a glycated hemoglobin A1c concentration of 6.5% (48 mmol/mol) or greater, on two consecutive tests may typically be considered to have type 2 diabetes mellitus, particularly when combined with an elevated plasma glucose level. An elevated plasma glucose level can be defined by one of three tests: (i) greater than or equal to 126 mg/dL (7.0 mmol/L) fasting plasma glucose level; (ii) greater than or equal to 200 mg/dL (11.1 mmol/L) plasma glucose level at 2 hours during oral glucose tolerance testing; (iii) a random plasma glucose level greater than or equal to 200 mg/dL with classic type 2 diabetes mellitus symptoms (i.e. frequent urination and extreme thirst); or (iv) currently taking medication for treatment of diabetes. For oral glucose tolerance testing, the patient fasts overnight, and fasting blood sugar level is measured. The patient then drinks a sugary liquid, and blood sugar levels are tested periodically for the next two hours.

Insulin resistance, as measured by HOMA-IR (homeostasis model assessment-estimated insulin resistance), may also be used to diagnose type 2 diabetes mellitus. As used herein, HOMA-IR refers to the Homeostasis Model Assessment for Insulin Resistance or "insulin resistance score," as reported by Matthews et al. Diabetologia 1985; 28:412-419. HOMA-IR can be computed with the formula: fasting plasma glucose (mmol/l) times fasting serum insulin (mU/l) divided by 22.5. Low HOMA-IR values indicate high insulin sensitivity, whereas high HOMA-IR values indicate low insulin sensitivity (i.e. insulin resistance).

Age is known as one of the multiple risk factors for cardiovascular disease, especially greater than 50 years of age if male and greater than 55 years of age if female.

A patient with systemic atherosclerosis includes any patient with (i) prior myocardial infarction or ischemic (non-hemorrhagic) stroke; (ii) coronary angiographic lesion of ≥60% stenosis in a major epicardial vessel or ≥50% left main stenosis; (iii) asymptomatic carotid disease with ≥70% carotid artery stenosis; (iv) symptomatic carotid disease with ≥50% carotid artery stenosis; (v) symptomatic lower extremity peripheral artery disease selected from intermittent claudication, rest pain, lower extremity ischemic ulceration, or major amputation with an ankle-brachial index ≤0.9 or other diagnostic testing (e.g., toe-brachial index, angiogram, or other imaging study); (vi) prior arterial revascularization procedure selected from coronary, carotid or peripheral angioplasty, stenting, bypass, atherectomy, or endarterectomy; or (vii) a combination thereof.

Hypertension can be defined as having a systolic blood pressure of greater than 120, 130, 140, or 160 mmHg and a diastolic blood pressure greater than 80, 90, or 100 mmHg.

The therapeutically effective amount of pemafibrate can be defined as a range of suitable doses on a daily basis. Thus, in one embodiment, the therapeutically effective amount is from 0.1 to 1.0 mg of pemafibrate or a pharmaceutically acceptable salt thereof, administered orally per day. In another embodiment the therapeutically effective amount is from 0.2 to 0.8 mg of pemafibrate or a pharmaceutically acceptable salt thereof, administered orally per day. In still another embodiment the therapeutically effective amount is 0.4 mg of pemafibrate or a pharmaceutically acceptable salt thereof, administered orally per day. These doses are preferably based on the weight of the free base of pemafibrate.

In a second additional embodiment, the invention provides a method of treating dyslipidemia in a patient with type 2 diabetes mellitus comprising administering to the patient a therapeutically effective amount of pemafibrate or a pharmaceutically acceptable salt thereof for a therapeutically effective period of time, wherein the patient has (a) an elevated fasting triglyceride level; (b) a low HDL-C concentration; and (c) controlled LDL-C levels.

In this second additional embodiment, elevated fasting triglyceride levels preferably refers to a fasting triglyceride level greater than 150, 160, 170, 175, 180, 190, 200, or 210 mg/dL triglycerides, with 175 or 200 mg/dL defining a particularly preferred cutoff value. The upper limit of the patient's fasting triglyceride levels is not particularly limited, but a cutoff value not greater than 500 mg/dL is preferred.

In this second additional embodiment, a low HDL-C level preferably refers to an HDL-C level at which the patient is at risk for an adverse cardiovascular event, and can be different depending on the patient's sex. In preferred embodiments the patient can be said to have a low HDL-C level if the patient has an HDL-C concentration less than 55, 50, 45, 40 or 35 mg/dL. A preferred cutoff value is ≤50 mg/dL if male or ≤55 mg/dL if female. A particularly preferred cutoff value is ≤40 mg/dL without regard to sex.

In this second additional embodiment, a patient with controlled LDL-C levels can refer to a patient having an LDL-C concentration ≤100 or 70 mg/dL, but preferably refers to a patient who is on concurrent statin therapy. A particularly preferred patient is: a) on concomitant moderate to high intensity statin therapy; b) on concomitant lipid-lowering therapy other than the concomitant moderate to high intensity statin therapy and has an LDL-C concentration ≤70 mg/dL; or c) statin-intolerant and has LDL-C concentration ≤100 mg/dL.

In this second additional embodiment, a patient with type 2 diabetes mellitus can be defined as a patient with: elevated glycated hemoglobin A1c levels and/or elevated plasma glucose levels. A patient having a glycated hemoglobin A1c concentration of 6.5% (48 mmol/mol) or greater, on two consecutive tests may typically be considered to have type 2 diabetes mellitus, particularly when combined with an elevated plasma glucose level. The elevated plasma glucose level can be defined by one of three tests: (i) greater than or equal to 126 mg/dL (7.0 mmol/L) fasting plasma glucose level; (ii) greater than or equal to 200 mg/dL (11.1 mmol/L) plasma glucose level at 2 hours during oral glucose tolerance testing; (iii) a random plasma glucose level greater than or equal to 200 mg/dL with classic type 2 diabetes mellitus symptoms; or (iv) currently taking medication for treatment of diabetes.

The therapeutically effective amount of pemafibrate for this second additional embodiment can be defined as a range of suitable doses on a daily basis. Thus, in one embodiment, the therapeutically effective amount is from 0.1 to 1.0 mg of pemafibrate or a pharmaceutically acceptable salt thereof, administered orally per day. In another embodiment the therapeutically effective amount is from 0.2 to 0.8 mg of pemafibrate or a pharmaceutically acceptable salt thereof, administered orally per day. In still another embodiment the therapeutically effective amount is 0.4 mg of pemafibrate or a pharmaceutically acceptable salt thereof, administered orally per day. These doses are preferably based on the weight of the free base of pemafibrate.

Other lipid values and their cutoff values can also be used to define the patients treated by this second additional embodiment, including elevated non-HDL-C, elevated Apo CIII, and elevated remnant cholesterol. In one embodiment, the patient's non-HDL-C concentration is greater than 130, 160, or 190 mg/dL. In another embodiment, the patient's remnant cholesterol level is greater than 5.0, 5.3, 5.6, or 5.9 mg/dL. In yet another embodiment, the patient's Apo CIII concentration is 5 to 20 mg/dL, for example, 5.8 to 10 mg/dL for male and 5.4 to 9.0 mg/dL for female.

Thus, in this second additional embodiment, the invention preferably provides a method of treating dyslipidemia in a patient with type 2 diabetes mellitus comprising administering to the patient a therapeutically effective amount of pemafibrate or a pharmaceutically acceptable salt thereof for a therapeutically effective period of time, wherein the patient has (a) a fasting TG concentration ≥175 mg/dL (2.26 mmol/L) and <500 mg/dL (5.64 mmol/L); (b) a HDL-C concentration ≤50 mg/dL if a male and ≤55 mg/dL if a female; and controlled LDL-C levels.

In this second additional embodiment, the invention most preferably provides a method of treating dyslipidemia in a patient with type 2 diabetes mellitus comprising administering to the patient a therapeutically effective amount of pemafibrate or a pharmaceutically acceptable salt thereof for a therapeutically effective period of time, wherein the patient has (a) a fasting TG concentration ≥200 mg/dL (2.26 mmol/L) and <500 mg/dL (5.64 mmol/L); (b) an HDL-C concentration ≤40 mg/dL (1.034 mmol/L); and LDL-C levels ≤100 mg/dL.

In a third additional embodiment, the invention provides a method of treating type 2 diabetes mellitus in a patient in need thereof comprising administering to the patient a therapeutically effective amount of pemafibrate or a pharmaceutically acceptable salt thereof for a therapeutically effective period of time, wherein the patient has (a) an elevated fasting triglyceride level; (b) a low HDL-C concentration; and (c) controlled LDL-C levels.

In this third additional embodiment, elevated fasting triglyceride levels preferably refers to a fasting triglyceride level greater than 150, 160, 170, 175, 180, 190, 200, or 210 mg/dL triglycerides, with 175 or 200 mg/dL defining a particularly preferred cutoff value. The upper limit of the patient's fasting triglyceride levels is not particularly limited, but a cutoff value not greater than 500 mg/dL is preferred.

In this third additional embodiment, a low HDL-C level preferably refers to an HDL-C level at which the patient is at risk for an adverse cardiovascular event, and can be different depending on the patient's sex. In preferred embodiments the patient can be said to have a low HDL-C level if the patient has an HDL-C concentration less than 55, 50, 45, 40 or 35 mg/dL. A preferred cutoff value is ≤50 mg/dL if male or ≤55 mg/dL if female. A particularly preferred cutoff value is ≤40 mg/dL without regard to sex.

In this third additional embodiment, a patient with controlled LDL-C levels can refer to a patient having an LDL-C concentration ≤100 or 70 mg/dL, but preferably refers to a patient who is on concurrent statin therapy. A particularly preferred patient is: a) on concomitant moderate to high intensity statin therapy; b) on concomitant lipid-lowering therapy other than the concomitant moderate to high intensity statin therapy and has an LDL-C concentration ≤70 mg/dL; or c) statin-intolerant and has LDL-C concentration ≤100 mg/dL.

In this third additional embodiment, a patient with type 2 diabetes mellitus can be defined as a patient with: elevated glycated hemoglobin A1c levels and/or elevated plasma glucose levels. A patient having a glycated hemoglobin A1c concentration of 6.5% (48 mmol/mol) or greater, on two consecutive tests may typically be considered to have type 2 diabetes mellitus, particularly when combined with an elevated plasma glucose level. The elevated plasma glucose level can be defined by one of three tests: (i) greater than or equal to 126 mg/dL (7.0 mmol/L) fasting plasma glucose level; (ii) greater than or equal to 200 mg/dL (11.1 mmol/L) plasma glucose level at 2 hours during oral glucose tolerance testing; (iii) a random plasma glucose level greater than or equal to 200 mg/dL with classic type 2 diabetes mellitus symptoms; or (iv) currently taking medication for treatment of diabetes.

The therapeutically effective amount of pemafibrate for this third additional embodiment can be defined as a range of suitable doses on a daily basis. Thus, in one embodiment, the therapeutically effective amount is from 0.1 to 1.0 mg of pemafibrate or a pharmaceutically acceptable salt thereof, administered orally per day. In another embodiment the therapeutically effective amount is from 0.2 to 0.8 mg of pemafibrate or a pharmaceutically acceptable salt thereof, administered orally per day. In still another embodiment the therapeutically effective amount is 0.4 mg of pemafibrate or a pharmaceutically acceptable salt thereof, administered orally per day. These doses are preferably based on the weight of the free base of pemafibrate.

Other lipid values and their cutoff values can also be used to define the patients treated by this third additional embodiment, including elevated non-HDL-C, elevated Apo CIII, and elevated remnant cholesterol. In one embodiment, the patient's non-HDL-C concentration is greater than 130, 160, or 190 mg/dL. In another embodiment, the patient's remnant cholesterol level is greater than 5.0, 5.3, 5.6, or 5.9 mg/dL. In yet another embodiment, the patient's Apo CIII concentration is 5 to 20 mg/dL, for example, 5.8 to 10 mg/dL for male and 5.4 to 9.0 mg/dL for female.

Thus, in this third additional embodiment, the invention preferably provides a method of treating dyslipidemia in a patient with type 2 diabetes mellitus comprising administering to the patient a therapeutically effective amount of pemafibrate or a pharmaceutically acceptable salt thereof for a therapeutically effective period of time, wherein the patient has (a) a fasting TG concentration ≥175 mg/dL (2.26 mmol/L) and <500 mg/dL (5.64 mmol/L); (b) a HDL-C concentration ≤50 mg/dL if a male and ≤55 mg/dL if a female; and controlled LDL-C levels.

In this third additional embodiment, the invention most preferably provides a method of treating dyslipidemia in a patient with type 2 diabetes mellitus comprising administering to the patient a therapeutically effective amount of pemafibrate or a pharmaceutically acceptable salt thereof for a therapeutically effective period of time, wherein the patient has (a) a fasting TG concentration ≥200 mg/dL (2.26 mmol/L) and <500 mg/dL (5.64 mmol/L); (b) a HDL-C concentration ≤40 mg/dL (1.034 mmol/L); and LDL-C levels ≤100 mg/dL.

In a fourth additional embodiment, the invention provides a method of treating cardiovascular disease or preventing cardiovascular events in a patient with type 2 diabetes mellitus comprising administering to the patient a therapeutically effective amount of pemafibrate or a pharmaceutically acceptable salt thereof for a therapeutically effective period of time, wherein the patient has (a) an elevated fasting triglyceride level; (b) a low HDL-C concentration; and (c) controlled LDL-C levels.

In this fourth additional embodiment, elevated fasting triglyceride levels preferably refers to a fasting triglyceride level greater than 150, 160, 170, 175, 180, 190, 200, or 210 mg/dL triglycerides, with 175 or 200 mg/dL defining a particularly preferred cutoff value. The upper limit of the patient's fasting triglyceride levels is not particularly limited, but a cutoff value not greater than 500 mg/dL is preferred.

In this fourth additional embodiment, a low HDL-C level preferably refers to an HDL-C level at which the patient is at risk for an adverse cardiovascular event, and can be different depending on the patient's sex. In preferred embodiments the patient can be said to have a low HDL-C level if the patient has an HDL-C concentration less than 55, 50, 45, 40 or 35 mg/dL. A preferred cutoff value is ≤50 mg/dL if male or ≤55 mg/dL if female. A particularly preferred cutoff value is ≤40 mg/dL without regard to sex.

In this fourth additional embodiment, a patient with controlled LDL-C levels can refer to a patient having an LDL-C concentration ≤100 or 70 mg/dL, but preferably refers to a patient who is on concurrent statin therapy. A particularly preferred patient is: a) on concomitant moderate to high intensity statin therapy; b) on concomitant lipid-lowering therapy other than the concomitant moderate to high intensity statin therapy and has an LDL-C concentration ≤70 mg/dL; or c) statin-intolerant and has LDL-C concentration ≤100 mg/dL.

In this fourth additional embodiment, a patient with type 2 diabetes mellitus can be defined as a patient with: elevated glycated hemoglobin A1c levels and/or elevated plasma glucose levels. A patient having a glycated hemoglobin A1c concentration of 6.5% (48 mmol/mol) or greater, on two consecutive tests may typically be considered to have type 2 diabetes mellitus, particularly when combined with an elevated plasma glucose level. The elevated plasma glucose level can be defined by one of three tests: (i) greater than or equal to 126 mg/dL (7.0 mmol/L) fasting plasma glucose level; (ii) greater than or equal to 200 mg/dL (11.1 mmol/L) plasma glucose level at 2 hours during oral glucose tolerance testing; (iii) a random plasma glucose level greater than or equal to 200 mg/dL with classic type 2 diabetes mellitus symptoms; or (iv) currently taking medication for treatment of diabetes.

The therapeutically effective amount of pemafibrate for this fourth additional embodiment can be defined as a range of suitable doses on a daily basis. Thus, in one embodiment, the therapeutically effective amount is from 0.1 to 1.0 mg of pemafibrate or a pharmaceutically acceptable salt thereof, administered orally per day. In another embodiment the therapeutically effective amount is from 0.2 to 0.8 mg of pemafibrate or a pharmaceutically acceptable salt thereof, administered orally per day. In still another embodiment the therapeutically effective amount is 0.4 mg of pemafibrate or a pharmaceutically acceptable salt thereof, administered orally per day. These doses are preferably based on the weight of the free base of pemafibrate.

Other lipid values and their cutoff values can also be used to define the patients treated by this fourth additional embodiment, including elevated non-HDL-C, elevated Apo CIII, and elevated remnant cholesterol. In one embodiment, the patient's non-HDL-C concentration is greater than 130, 160, or 190 mg/dL. In another embodiment, the patient's remnant cholesterol level is greater than 5.0, 5.3, 5.6, or 5.9 mg/dL. In yet another embodiment, the patient's Apo CIII concentration is 5 to 20 mg/dL, for example, 5.8 to 10 mg/dL for male and 5.4 to 9.0 mg/dL for female.

Thus, in this fourth additional embodiment, the invention preferably provides a method of treating dyslipidemia in a patient with type 2 diabetes mellitus comprising administering to the patient a therapeutically effective amount of pemafibrate or a pharmaceutically acceptable salt thereof for a therapeutically effective period of time, wherein the patient has (a) a fasting TG concentration ≥175 mg/dL (2.26 mmol/L) and <500 mg/dL (5.64 mmol/L); (b) a HDL-C concentration ≤50 mg/dL if a male and ≤55 mg/dL if a female; and controlled LDL-C levels.

In this fourth additional embodiment, the invention most preferably provides a method of treating dyslipidemia in a patient with type 2 diabetes mellitus comprising administering to the patient a therapeutically effective amount of pemafibrate or a pharmaceutically acceptable salt thereof for a therapeutically effective period of time, wherein the patient has (a) a fasting TG concentration ≥200 mg/dL (2.26 mmol/L) and <500 mg/dL (5.64 mmol/L); (b) a HDL-C concentration ≤40 mg/dL (1.034 mmol/L); and LDL-C levels ≤100 mg/dL.

In a fifth additional embodiment, the invention provides a method of prolonging the time to first occurrence of:
a) any component of the primary endpoint in subgroups of subjects defined at baseline by: sex; presence or absence of established CVD; and baseline lipid lowering therapy as defined hierarchically by:

i) receiving treatment with a stable dose (i.e. for at least 12 weeks) of a qualifying moderate to high intensity statin; or
ii) statin intolerant and have evidence of LDL<100 mg/dl (2.59 mmol/L) by local laboratory determination within the previous 12 months; or
iii) have evidence of LDL-C<70 mg/dl (1.81 mmol/L) by local laboratory determination within the previous 12 months if untreated or on stable dosing (i.e. for at least 12 weeks) of another lipid-lowering regimen including a PCSK9 inhibitor.

b) any component of nonfatal MI, nonfatal ischemic stroke, hospitalization of for unstable angina requiring unplanned coronary revascularization, CV death, or any coronary revascularization;

c) any component of nonfatal MI, nonfatal ischemic stroke, hospitalization for unstable angina requiring unplanned coronary revascularization, or all-cause mortality;

d) any component of nonfatal MI, nonfatal ischemic stroke, CV death, any coronary revascularization, or hospitalization for heart failure;

e) any component of nonfatal MI, nonfatal stroke (any), CV death, or hospitalization for unstable angina requiring unplanned coronary revascularization;

f) individual components of the primary endpoint, nonfatal stroke (any), all cause mortality, and hospitalization for heart failure;

g) diabetic retinopathy, as assessed by use of retinal laser treatment, anti-vascular endothelial growth factor therapy, or vitrectomy due to development of and/or deterioration in diabetic retinopathy;

h) diabetic nephropathy, as assessed by an increase in microalbumin/creatinine ratio to >30 mg/g among those without microalbuminuria at baseline, and categorical change from baseline albuminuria (normo-, micro-, or macroalbuminuria), doubling of creatinine from baseline, creatinine level >6.0 mg/dl, glomerular filtration rate (GFR) <15 ml/ml, or initiation of renal replacement therapy (dialysis or transplant), among all subjects; and i) peripheral artery disease, defined as incidence of lower-extremity revascularization, intermittent claudication, rest pain, lower-extremity ischemic ulceration, or amputation with either ankle brachial index <0.9 or other diagnostic testing (e.g., angiogram, toe-brachial index, or imaging study), wherein the method comprises administering to the subjects a therapeutically effective amount of pemafibrate or a pharmaceutically acceptable salt thereof.

In a sixth additional embodiment, the invention provides a method of prolonging the time to first occurrence of:
a) any component of the 3-component composite endpoint of non-fatal MI, non-fatal stroke, or cardiovascular death;
b) any component of the primary endpoint or hospitalization for heart failure;
c) any component of the primary endpoint or all-cause mortality;
d) any component of the primary endpoint, any coronary revascularization, or hospitalization for heart failure; or
e) any new or worsening peripheral artery disease, defined as incidence of lower extremity revascularization, intermittent claudication, rest pain, lower extremity ischemic ulceration, or major amputation with either ankle-brachial index ≤0.9 or other diagnostic testing (e.g., toe-brachial index, angiogram, or other imaging study).

Pemafibrate achieves these benefits without any significant safety concerns, even when co-administered with a statin.

The dosing of the pemafibrate is preferably defined based on route of administration, dose, and length of treatment. The preferred route of administration is oral. Pemafibrate can be administered to a patient in the fed or fasting state.

The therapeutically effective amount of pemafibrate can be defined as a range of suitable doses on a daily basis. Thus, in one embodiment the therapeutically effective amount is from 0.1 to 1.0 mg of pemafibrate or a pharmaceutically acceptable salt thereof, administered orally per day. In another embodiment the therapeutically effective amount is from 0.2 to 0.8 mg of pemafibrate or a pharmaceutically acceptable salt thereof, administered orally per day. In still another embodiment the therapeutically effective amount is 0.4 mg of pemafibrate or a pharmaceutically acceptable salt thereof, administered orally per day. These doses are preferably based on the weight of the free base of pemafibrate.

The dose of pemafibrate can be administered as one dose per day or in two, three or four evenly divided doses per day.

In some embodiments, pemafibrate can be administered for a therapeutically effective period of time. The therapeutically effective period of time refers to the period of time necessary to prevent the occurrence of cardiovascular events, and varies depending on the conditions of a patient being treated, extent and severity of risk factors, and other factors such as the patient's age. The therapeutically effective period of time generally equates to three or more months of treatment, six or more months, one or more years, two or more years, three or more years, or four or more years.

In some embodiments, lipid values and these risk factors can be combined in any manner to define patient populations treatable by the methods of the present invention, and that any of the cutoff value provided for a particular parameter can be applied to define the patient. Thus, in one embodiment, the patient can have high TG and/or low HDL-C. In another embodiment, the patient can have high TG and/or low HDL-C, and one or more selected from the group consisting of controlled LDL-C, systemic atherosclerosis, age (male ≥50 or female ≥55), type 2 diabetes mellitus, elevated non-HDL-C, elevated Apo CIII, elevated remnant cholesterol and systemic atherosclerosis.

Other embodiments of the invention may be apparent to those skilled in the art from consideration of the specification and practice of the invention disclosed herein. It is intended that the specification and examples be considered as exemplary only, with a true scope and spirit of the invention being indicated by the following claims.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1 Treatment of Dyslipidemia with Pemafibrate as Add-on to Statin Therapy A placebo-controlled, randomized, double-blind parallel-group study was performed to evaluate the treatment effect of pemafibrate in dyslipidemia patients on concurrent statin therapy. Dyslipidemia patients on a stable dose of statin therapy (atorvastatin, rosuvastatin or simvastatin) were randomized to one (1) of seven (7) treatment groups: once daily [QD] pemafibrate 0.1 mg, 0.2 mg, or 0.4 mg; twice daily [BID] pemafibrate 0.05 mg, 0.1 mg, or 0.2 mg; or placebo, for 12 weeks of pemafibrate treatment, and were followed for an additional 2 weeks thereafter.

Patients were required to have statin controlled LDL-C (≤10 mg/dL above the NCEP ATP III target of 100 mg/dL) or on a maximum tolerated dose of statin, but residual dyslipidemia (TG ≥175 and ≤500 mg/dL; HDL-C≤50 mg/dL for male and ≤55 mg/dL for female. Differences in changes of TG, non-HDL-C, Apo CIII, and remnant-C between treatment groups were evaluated for significance. Overall, 408 patients were randomized to treatment, and 375 patients (91.9%) completed the study. There were no significant differences between the 7 treatment groups at baseline. 99% of patients were white Caucasian, 31.9% had a history of coronary heart disease, 37.8% had type 2 diabetes mellitus; intensity of statin treatment was high in 46.3% of patients, moderate in 48.1%. The results of the study are depicted in FIGS. 1A-1D.

The following observations also were made:

Pemafibrate significantly reduced TG levels in all treatment groups after 12 weeks (FIG. 1A).

Non-HDL-C levels were significantly reduced at 0.2 mg BID and 0.2 mg QD doses (FIG. 1B).

LDL-C levels were significantly increased at 0.1 mg BID (22.46% vs. placebo), 0.2 mg BID (24.25%), and 0.4 mg QD (18.74%), with no significant change in total Apo B at any dose.

Significant increases in HDL-C (7.35% to 10.95% vs. placebo) were observed at all doses except the 0.1 mg QD dose.

There were dose-dependent reductions with BID dosing for TG, non-HDL-C, Apo CIII (FIG. 1C), remnant-C (FIG. 1D), and Apo B48 (−40.8% to −63.4%) that reached statistical significance for both TG and non-HDL-C at 0.2 mg BID; the effects of QD dosing were more variable across doses.

Adverse events occurred in 56.7% of patients on placebo vs. 46.4% of those on pemafibrate, with no relationship to dose. No other safety concerns were observed.

Example 2 Retrospective Analysis of Type 2 Diabetes Patients

A post-hoc analysis of patients with type 2 diabetes mellitus (HbA1c≤10%) who participated in the study described in Example 1, was undertaken to determine the treatment effect of pemafibrate in diabetes patients. Overall, 161 type 2 diabetes mellitus patients were randomized and 154 patients completed treatment. 99.4% were white Caucasian, and 35.7% had a history of CHD; intensity of statin therapy was high in 45.5% of patients, moderate in 49.4%. The results of the analysis are reported in FIGS. 2A-2D.

Tables 1-4 also report the results of the analyses, and compare the results to the results obtained for the general residual dyslipidemia population studied in Example 1.

TABLE 1

(TG Reduction Relative to Placebo)

| Dose | Residual Dyslipidemia Population | Diabetic Sub-Population with Residual Dyslipidemia |
|---|---|---|
| 0.05 mg BID | −36.1 | −47.0 |
| 0.1 mg BID | −45.8 | −67.4 |
| 0.2 mg BID | −54.4 | −56.1 |
| 0.1 mg QD | −34.0 | −44.7 |
| 0.2 mg QD | −37.7 | −48.1 |
| 0.4 mg QD | −42.7 | −47.9 |

TABLE 2

(Non HDL-C Reduction Relative to Placebo)

| Dose | Residual Dyslipidemia Population | Diabetic Sub-Population with Residual Dyslipidemia |
|---|---|---|
| 0.05 mg BID | −6.8 | −14.2 |
| 0.1 mg BID | −7.4 | −17.3 |
| 0.2 mg BID | −8.9 | −10.9 |
| 0.1 mg QD | −5.2 | −5.5 |
| 0.2 mg QD | −9.1 | −15.3 |
| 0.4 mg QD | −7.8 | −10.3 |

TABLE 3

(Apo CIII Reduction Relative to Placebo)

| Dose | Residual Dyslipidemia Population | Diabetic Sub-Population with Residual Dyslipidemia |
|---|---|---|
| 0.05 mg BID | −15.5 | −26.1 |
| 0.1 mg BID | −28.7 | −37.3 |
| 0.2 mg BID | −36.0 | −39.7 |
| 0.1 mg QD | −17.1 | −23.8 |
| 0.2 mg QD | −24.3 | −35.4 |
| 0.4 mg QD | −23.8 | −32.4 |

TABLE 4

(Remnant-C Reduction Relative to Placebo)

| Dose | Residual Dyslipidemia Population | Diabetic Sub-Population with Residual Dyslipidemia |
|---|---|---|
| 0.05 mg BID | −35.6 | −55.6 |
| 0.1 mg BID | −48.8 | −81.8 |
| 0.2 mg BID | −58.0 | −70.7 |
| 0.1 mg QD | −39.9 | −62.1 |
| 0.2 mg QD | −45.9 | −66.3 |
| 0.4 mg QD | −45.5 | −58.7 |

As can be seen, pemafibrate consistently reduced TG, non-HDL-C, Apo CIII, and remnant cholesterol values more in type 2 diabetes patients than in the general dyslipidemia population treated in Example 1. This is opposite the results reported in the VA-HIT trial, wherein the authors reported "It is also interesting to note that the clinical efficacy of gemfibrozil was more pronounced in subjects with diabetes than those without despite the fact that gemfibrozil's effects on lipids was less pronounced (i.e. lesser reduction in triglyceride level and lesser increase in HDL-C level in diabetic compared to non-diabetic persons). Other studies have also noted a possible lesser effect of gemfibrozil on HDL-C and triglyceride levels in persons with diabetes compared with those without." Rubins H et al, *Diabetes, Plasma Insulin, and Cardiovascular Disease, Subgroup Analysis from the Department of Veterans' Affairs High Density Lipoprotein Intervention Trial (VA-HIT)*. ARCH INTERNAL MEDICINE 2002; 162:2597-2604.

The following observations also were made:
Pemafibrate significantly reduced TG levels across all doses (FIG. 2A).
Decreases in non-HDL-C were less consistent across treatment groups (FIG. 2B);
pemafibrate significantly increased BQ LDL-C at 0.2 mg BID (1.8%) and 0.1 mg QD (6.7%), with no significant change in total Apo B at any dose.
Pemafibrate significantly reduced Apo CIII (FIG. 2C), remnant-C (FIG. 2D), and
Apo B48 levels at all doses.
Significant increases were seen for HDL-C at doses of 0.05 mg BID (11.39%), 0.1 mg BID (11.94%), and 0.2 mg QD (9.48%).
With the exception of Apo CIII and BQ LDL-C levels, changes in lipid parameters were not further increased at doses higher than 0.1 mg BID.
57.7% of placebo patients reported an adverse event compared with 25.0% to 71.4% of pemafibrate-treated patients, with no relationship to dose.

Example 3 Effectiveness of Pemafibrate as Add-on to Pitavastatin Therapy

A double-blind parallel-group study was undertaken to determine the effectiveness of pemafibrate when added to an existing statin regimen. A total of 188 patients with fasting high TG ($\geq$200, <1000 mg/dL) and non-HDL-C ($\geq$150 mg/dL), treated with pitavastatin (once daily, 2 mg/day) were randomized to 12-week treatment groups; placebo (n=46), twice-daily pemafibrate 0.1 (n=45), 0.2 (n=49) and 0.4 mg/day (n=48). The primary endpoint was the percentage change in TG from baseline and incidence of adverse drug reactions (ADRs) and adverse events (AEs).

The results of the study are reported in FIGS. 3A-3D and summarized as follows. Fasting TG reduction was as follows; placebo: −6.9%, pemafibrate 0.1, 0.2 and 0.4 mg: −46.1%, −53.4% and −52.0%. All pemafibrate groups had significant reductions compared with placebo (P<0.001). Fasting non-HDL-C reductions were −5.9% with placebo and −11.3, −14.1 and −13.3% with pemafibrate 0.1, 0.2 and 0.4 mg, respectively. Significant increase in HDL-C, and reductions in VLDL-C, remnant lipoprotein cholesterol and Apo CIII compared to placebo were found in all pemafibrate groups (P<0.01). Although pemafibrate had a neutral effect on total LDL-C, HPLC analysis revealed a significant reduction of very small LDL-C with pemafibrate compared to the placebo group (P<0.05). Moreover, the highest dose of pemafibrate (0.4 mg/day) showed significant reductions in fasting plasma glucose and HOMA-IR compared to placebo (P=0.003 and 0.019, respectively).

Example 4. Phase III Clinical Trial to Confirm the Ability of Pemafibrate to Prevent Cardiovascular Events in Residual Dyslipidemia Patients A phase III clinical trial has been approved by the United States Food and Drug Administration to confirm the ability of 2.0 mg BID pemafibrate to prevent cardiovascular events in residual dyslipidemia patients. The trial has the following design:

Purpose: The primary objective of the study is to confirm that pemafibrate administered twice daily will delay the time to first occurrence of any component of the clinical composite endpoint of:
nonfatal Myocardial Infarction (MI)
nonfatal ischemic stroke
hospitalization for unstable angina requiring unplanned coronary revascularization; or
Cardio Vascular (CV) death.
Condition: Type 2 Diabetes with Dyslipidemia
Intervention: Pemafibrate (0.2 mg tablet administered twice daily) or Matching Placebo (administered twice daily)
Study Type: Interventional
Study Design: Allocation: Randomized
Intervention Model: Parallel Assignment
Masking: Participant, Care Provider, Investigator, Outcomes Assessor
Primary Purpose: Prevention
Primary Outcome Measures:
Number of patients with first occurrence of nonfatal MI, nonfatal ischemic stroke, hospitalization for unstable angina requiring unplanned coronary revascularization, or CV death.
Secondary Outcome Measures:
Any component of the 3-component composite endpoint of non-fatal MI, non-fatal stroke, or cardiovascular death
Any component of the primary endpoint or hospitalization for HF
Any component of the primary endpoint or all-cause mortality
Any component of the primary endpoint, any coronary revascularization, or hospitalization for HF
Any new or worsening PAD, defined as incidence of lower extremity revascularization, intermittent claudication, rest pain, lower extremity ischemic ulceration, or major amputation with either ankle-brachial index ≤0.9 or other diagnostic testing (e.g., toe-brachial index, angiogram, or other imaging study)
The change from Screening/Enrollment Visit (Visit 1) to Month 4 Visit (Visit 5) for the following lipid biomarkers: Total cholesterol (TC), Triglyceride(s) (TG), High-density lipoprotein cholesterol (HDL-C), non-HDL-C (calculated), Very low-density lipoprotein cholesterol (VLDL-C) (calculated), ApoA1, ApoC3, and ApoE
The change from Randomization Visit (Visit 2) to Month 6 Visit (Visit 6) for nonfasting remnant cholesterol
VLDL-C will be calculated as TC minus HDL-C *minus* LDL-C, where LDL-C is measured by a direct homogenous method.
Ages Eligible for Study: 18 Years and older (Adult, Senior)
Sexes Eligible for Study: All
Accepts Healthy Volunteers: No
Inclusion Criteria:
1. Fasting TG ≥200 mg/dL (2.26 mmol/L) and <500 mg/dL (5.65 mmol/L) at Visit 1 (Screening/Enrollment Visit) or Visit 1.1 (Retest)
2. HDL-C≤40 mg/dL (1.03 mmol/L) at Visit 1 (Screening/Enrollment Visit) or Visit 1.1 (Retest)
3. Controlled LDL defined by:
receiving treatment with a stable dose (for at least 12 weeks [84 days]) of a qualifying moderate to high-intensity statin (atorvastatin ≥40 mg/day, rosuvastatin ≥20 mg/day, simvastatin ≥40 mg/day, or pitavastatin=4 mg/day)*, or have evidence of LDL-C≤70 mg/dl (1.81 mmol/L) by local laboratory determination within the previous 12 months#, or have evidence of LDL≤100 mg/dl (2.59 mmol/L) by local laboratory determination within the previous 12 months if statin intolerant+.

Participants enrolled on simvastatin >40 mg/day must have been taking and tolerating that dose for at least 12 months.

If untreated or on stable dosing (ie, for at least 12 weeks) of another lipid-lowering regimen that may include a statin with or without ezetimibe and/or a PCSK9 inhibitor Statin intolerance is defined as: the inability to tolerate at least 2 statins: 1 statin at the lowest daily starting dose (defined as rosuvastatin 5 mg, atorvastatin 10 mg, simvastatin 10 mg, lovastatin 20 mg, pravastatin 40 mg, fluvastatin 40 mg or pitavastatin 2 mg), AND another statin at any dose, due to skeletal muscle-related symptoms, other than those due to strain or trauma, such as pain, aches, weakness, or cramping, that begins or increases during statin therapy and stops when statin therapy is discontinued. Participants not receiving a daily regimen of a statin (e.g., 1-3 times weekly) could also be considered "statin intolerant" if they cannot tolerate a cumulative weekly statin dose of 7 times the lowest approved tablet size, and the criteria outlined above are also met.

4. Type 2 diabetes of longer than 12 weeks' duration documented/confirmed in medical records, for example: local laboratory evidence through medical record review of elevated HbA1c (≥6.5% [48 mmol/mol]), elevated plasma glucose (fasting ≥126 mg/dL [7.0 mmol/L], 2-hour ≥200 mg/dL [11.1 mmol/L] during oral glucose tolerance testing, or random value ≥200 mg/dL with classic symptoms, or currently taking medication for treatment of diabetes); AND either
   a. Age ≥50 years if male or ≥55 years if female (primary prevention cohort); OR
   b. Age ≥18 years and established systemic atherosclerosis (secondary prevention cohort), defined as any 1 of the following:
      i. Prior MI or ischemic (non-hemorrhagic) stroke
      ii. Coronary angiographic lesion of ≥60% stenosis in a major epicardial vessel or ≥50% left main stenosis
      iii. Asymptomatic carotid disease with ≥70% carotid artery stenosis
      iv. Symptomatic carotid disease with ≥50% carotid artery stenosis
      v. Symptomatic lower extremity PAD (i.e., intermittent claudication, rest pain, lower extremity ischemic ulceration, or major amputation with either ankle-brachial index ≤0.9 or other diagnostic testing [e.g., toe-brachial index, angiogram, or other imaging study])
      vi. Prior arterial revascularization procedure (including coronary, carotid, or peripheral angioplasty/stenting, bypass, or atherectomy/endarterectomy)

Exclusion Criteria:
1. Current or planned use of fibrates or agents with PPAR-α agonist activity (e.g., saroglitazar) within 6 weeks (42 days) of Visit 1 (Screening/Enrollment Visit). Note: PPAR-γ agonists (e.g., glitazones such as pioglitazone and rosiglitazone) are allowed 2. Known sensitivity to PPAR-α agonists or tablet excipients 3. Initiation of, or change in, current TG-lowering therapy within 12 weeks of Visit 1 (if applicable). Note: TG-lowering therapy is defined as niacin >100 mg/day or dietary supplements or prescription omega-3 fatty acids >1 g/day 4. Type 1 diabetes mellitus Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

The invention claimed is:

1. A method of preventing an adverse cardiovascular event in a patient with type 2 diabetes mellitus comprising administering to the patient a therapeutically effective amount of pemafibrate therapy, wherein:
   a) prior to commencing the pemafibrate therapy the patient has an LDL-C concentration ≤70 mg/dL and is on stable statin therapy selected from low to high intensity statin therapy;
   b) the patient has an HDL-C concentration ≤40 mg/dL prior to commencing the pemafibrate therapy;
   c) the patient has a fasting TG concentration ≥200 mg/dL and <500 mg/dL prior to commencing the pemafibrate therapy;
   d) the patient continues the statin therapy after commencing the pemafibrate therapy; and
   e) the method prevents the cardiovascular event without decreasing LDL-C concentrations in the patient.

2. The method of claim 1, wherein said patient does not have systemic atherosclerosis and does not have cardiovascular disease.

3. The method of claim 1, wherein said patient is ≥50 years of age without systemic atherosclerosis if a man, ≥55 years of age without systemic atherosclerosis if a woman, and said method prevents ischemic stroke, hospitalization for unstable angina requiring unplanned coronary revascularization, or cardiovascular death.

4. The method of claim 1, wherein said patient is at risk for an ischemic stroke, and said method prevents said ischemic stroke, wherein said method is practiced for a therapeutically effective period of time equaling three years.

5. The method of claim 1, wherein said patient is at risk for coronary revascularization and said method prevents said coronary revascularization, wherein said method is practiced for a therapeutically effective period of time equaling three years.

6. The method of claim 1, wherein said patient is at risk for cardiovascular death and said method prevents said cardiovascular death, wherein said method is practiced for a therapeutically effective period of time equaling three years.

7. The method of claim 1, wherein said patient has an HDL-C concentration of >35 mg/dL prior to commencing the pemafibrate therapy.

8. The method of claim 1, wherein said patient has an age ≥50 years without systemic atherosclerosis if male or ≥55 years without systemic atherosclerosis if female.

9. The method of claim 1, wherein said stable statin therapy comprises atorvastatin ≥40 mg/day (based on the weight of the free base).

10. The method of claim 1, wherein said stable statin therapy comprises rosuvastatin ≥20 mg/day (based on the weight of the calcium salt).

11. The method of claim 1, wherein said stable statin therapy comprises simvastatin ≥40 mg/day (based on the weight of the free base).

12. The method of claim 1, wherein said stable statin therapy comprises pitavastatin ≥4 mg/d (based on the weight of the free base).

13. The method of claim 1, wherein the pemafibrate therapy comprises oral administration of 0.4 mg per day of pemafibrate or a pharmaceutically acceptable salt thereof based on the weight of the free base.

14. The method of claim 1, wherein, for step e), the method prevents the cardiovascular event without decreasing LDL-C concentrations in the patient during the first 12 weeks of pemafibrate administration.

15. The method of claim 1, wherein said patient has systemic atherosclerosis or cardiovascular disease.

16. The method of claim 1, wherein the statin therapy is high intensity statin therapy.

17. The method of claim 1, wherein the statin therapy is high intensity statin therapy and said patient does not have systemic atherosclerosis and does not have cardiovascular disease.

18. The method of claim 1, wherein the statin therapy is high intensity statin therapy and said patient has systemic atherosclerosis or cardiovascular disease.

19. The method of claim 1, wherein the statin therapy is low or moderate intensity statin therapy.

20. The method of claim 1, wherein the statin therapy is low or moderate intensity statin therapy and said patient has systemic atherosclerosis or cardiovascular disease.

21. The method of claim 1, wherein the statin therapy is low or moderate intensity statin therapy and said patient does not have systemic atherosclerosis and does not have cardiovascular disease.

22. The method of claim 1, further comprising administering a therapeutically effective amount of a lipid lowering therapy selected from ezetimibe, probucol, niacin, cholestyramine, eicosapentaenoic acid (EPA), and docosahexaenoic acid (DHA).

23. The method of claim 1, further comprising administering a therapeutically effective amount of a cardiovascular drug selected from an angiotensin converting-enzyme inhibitor, an angiotensin-receptor blocker, aspirin, a beta-blocker, a nitrate, and a thiazide diuretic.

24. The method of claim 1, further comprising administering a therapeutically effective amount of ezetimibe or a proprotein convertase subtilisin/kexin type 9 (PCSK9) inhibitor.

25. The method of claim 1, further comprising administering a therapeutically effective amount of a diabetes medication selected from an alpha-glucosidase inhibitor, a biguanide, a dopamine agonist, a DPP-4 inhibitor, a glucagon-like peptide, a meglitinide, a sodium glucose transporter (SGLT) 2 inhibitor, a sulfonylurea, and a thiazolidinedione.

26. The method of claim 1, further comprising administering a therapeutically effective amount of a diabetes medication targeting a HbA1c concentration of less than 6%.

27. The method of claim 1, wherein the patient is at risk for rhabdomyolysis as shown by elevated creatinine kinase.

28. The method of claim 1, wherein the patient has renal insufficiency.

29. The method of claim 1, wherein the patient has renal failure.

* * * * *